(12) United States Patent
Chen et al.

(10) Patent No.: US 12,702,755 B1
(45) Date of Patent: Aug. 11, 2026

(54) MODEL PREDICTIVE CONTROL IN A CLOSED LOOP CONTROL SYSTEM FOR CONTINUOUS GLUCOSE MONITORING

(71) Applicant: Willow Laboratories, Inc., Irvine, CA (US)

(72) Inventors: Jesse Chen, Foothill Ranch, CA (US); Kevin Hughes Pauley, Lake Forest, CA (US); Yu Zhao, Irvine, CA (US); Hung The Vo, Fountain Valley, CA (US)

(73) Assignee: Willow Laboratories, Inc., Irvine, CA (US)

( * ) Notice: Subject to any disclaimer, the term of this patent is extended or adjusted under 35 U.S.C. 154(b) by 799 days.

(21) Appl. No.: 17/668,957

(22) Filed: Feb. 10, 2022

Related U.S. Application Data

(60) Provisional application No. 63/149,089, filed on Feb. 12, 2021.

(51) Int. Cl.
*A61M 5/172* (2006.01)
*A61M 5/142* (2006.01)
*H04L 67/141* (2022.01)

(52) U.S. Cl.
CPC ...... *A61M 5/1723* (2013.01); *A61M 5/14244* (2013.01); *A61M 2205/3584* (2013.01); *A61M 2205/502* (2013.01); *A61M 2230/201* (2013.01)

(58) Field of Classification Search
CPC ............ A61M 5/14244; A61M 5/1723; A61M 2205/3584; A61M 2205/502; A61M 2230/201; H04L 43/00; H04L 67/55; H04L 67/14; H04L 67/141; H04L 65/1069; G06F 11/34; H04W 76/00; H04W 76/10
USPC .......................................................... 709/227
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |

(Continued)

FOREIGN PATENT DOCUMENTS

| | | | | |
|---|---|---|---|---|
| CN | 106264549 A * | 1/2017 | | |
| WO | WO-2018125841 A1 * | 7/2018 | ............... | A43B 3/34 |

(Continued)

OTHER PUBLICATIONS

US 2024/0016391 A1, 01/2024, Lapotko et al. (withdrawn)

(Continued)

*Primary Examiner* — Alina A Boutah

(74) *Attorney, Agent, or Firm* — Knobbe, Martens, Olson & Bear, LLP

(57) ABSTRACT

A system which provides closed loop insulin administration is disclosed. A closed loop insulin administration system (Continued)

which bases insulin administration on accurate glucose measurements may improve a patient's quality of life.

18 Claims, 16 Drawing Sheets

(56) References Cited

U.S. PATENT DOCUMENTS

D362,063 S 9/1995 Savage et al.
D363,120 S 10/1995 Savage et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,561,275 A 10/1996 Savage et al.
5,590,649 A 1/1997 Caro et al.
5,602,924 A 2/1997 Durand et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,890,929 A 4/1999 Mills et al.
5,919,134 A 7/1999 Diab
5,987,343 A 11/1999 Kinast
5,997,343 A 12/1999 Mills et al.
6,002,952 A 12/1999 Diab et al.
6,010,937 A 1/2000 Karam et al.
6,027,452 A 2/2000 Flaherty et al.
6,040,578 A 3/2000 Malin et al.
6,066,204 A 5/2000 Haven
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,152,754 A 11/2000 Gerhardt et al.
6,184,521 B1 2/2001 Coffin, IV et al.
6,232,609 B1 5/2001 Snyder et al.
6,241,683 B1 6/2001 Macklem et al.
6,255,708 B1 7/2001 Sudharsanan et al.
6,280,381 B1 8/2001 Malin et al.
6,285,896 B1 9/2001 Tobler et al.
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,606,511 B1 8/2003 Ali et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,697,656 B1 2/2004 Al-Ali
6,697,658 B2 2/2004 Al-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
6,850,787 B2 2/2005 Weber et al.
6,850,788 B2 2/2005 Al-Ali
6,876,931 B2 4/2005 Lorenz et al.
6,920,345 B2 7/2005 Al-Ali et al.
6,934,570 B2 8/2005 Kiani et al.
6,943,348 B1 9/2005 Coffin, IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
7,225,006 B2 5/2007 Al-Ali et al.
RE39,672 E 6/2007 Shehada et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.

(56) References Cited

U.S. PATENT DOCUMENTS 7,729,733 B2 6/2010 Al-Ali et al.
7,761,127 B2 7/2010 Al-Ali et al.
7,764,982 B2 7/2010 Dalke et al.
D621,516 S 8/2010 Kiani et al.
7,791,155 B2 9/2010 Diab
RE41,912 E 11/2010 Parker
7,880,626 B2 2/2011 Al-Ali et al.
7,909,772 B2 3/2011 Popov et al.
7,919,713 B2 4/2011 Al-Ali et al.
7,937,128 B2 5/2011 Al-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,130,105 B2 3/2012 Al-Ali et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,255,026 B1 8/2012 Al-Ali
8,265,723 B1 9/2012 McHale et al.
8,274,360 B2 9/2012 Sampath et al.
8,280,473 B2 10/2012 Al-Ali
8,315,683 B2 11/2012 Al-Ali et al.
RE43,860 E 12/2012 Parker
8,346,330 B2 1/2013 Lamego
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Al-Ali
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,652,060 B2 2/2014 Al-Ali
8,666,468 B1 3/2014 Al-Ali
8,670,811 B2 3/2014 O'Reilly
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,745,247 B1 * 6/2014 Park ...................... G08C 17/02 709/200
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
8,852,094 B2 10/2014 Al-Ali et al.
8,852,994 B2 10/2014 Wojtczuk et al.
8,897,847 B2 11/2014 Al-Ali
8,911,377 B2 12/2014 Al-Ali
8,989,831 B2 3/2015 Al-Ali et al.
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,138,180 B1 9/2015 Coverston et al.
9,153,112 B1 10/2015 Kiani et al.
9,192,329 B2 11/2015 Al-Ali
9,192,351 B1 11/2015 Telfort et al.
9,195,385 B2 11/2015 Al-Ali et al.
9,211,095 B1 12/2015 Al-Ali
9,218,454 B2 12/2015 Kiani et al.
9,245,668 B1 1/2016 Vo et al.
9,267,572 B2 2/2016 Barker et al.
9,277,880 B2 3/2016 Poeze et al.
9,307,928 B1 4/2016 Al-Ali et al.
9,323,894 B2 4/2016 Kiani
D755,392 S 5/2016 Hwang et al.
9,326,712 B1 5/2016 Kiani
9,392,945 B2 7/2016 Al-Ali et al.
9,408,542 B1 8/2016 Kinast et al.
9,436,645 B2 9/2016 Al-Ali et al.
9,445,759 B1 9/2016 Lamego et al.
9,474,474 B2 10/2016 Lamego et al.
9,480,435 B2 11/2016 Olsen
9,510,779 B2 12/2016 Poeze et al.
9,517,024 B2 12/2016 Kiani et al.
9,532,722 B2 1/2017 Lamego et al.
9,560,996 B2 2/2017 Kiani
9,579,039 B2 2/2017 Jansen et al.
9,622,692 B2 4/2017 Lamego et al.
D788,312 S 5/2017 Al-Ali et al.
9,649,054 B2 5/2017 Lamego et al.
9,697,928 B2 7/2017 Al-Ali et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,749,232 B2 8/2017 Sampath et al.
9,750,442 B2 9/2017 Olsen
9,750,461 B1 9/2017 Telfort
9,775,545 B2 10/2017 Al-Ali et al.
9,778,079 B1 10/2017 Al-Ali et al.
9,782,077 B2 10/2017 Lamego et al.
9,787,568 B2 10/2017 Lamego et al.
9,808,188 B1 11/2017 Perea et al.
9,839,379 B2 12/2017 Al-Ali et al.
9,839,381 B1 12/2017 Weber et al.
9,847,749 B2 12/2017 Kiani et al.
9,848,800 B1 12/2017 Lee et al.
9,861,298 B2 1/2018 Eckerbom et al.
9,861,305 B1 1/2018 Weber et al.
9,877,650 B2 1/2018 Muhsin et al.
9,891,079 B2 2/2018 Dalvi
9,924,897 B1 3/2018 Abdul-Hafiz
9,936,917 B2 4/2018 Poeze et al.

(56) References Cited

U.S. PATENT DOCUMENTS 9,955,937 B2 5/2018 Telfort
9,965,946 B2 5/2018 Al-Ali et al.
D820,865 S 6/2018 Muhsin et al.
9,986,952 B2 6/2018 Dalvi et al.
D822,215 S 7/2018 Al-Ali et al.
D822,216 S 7/2018 Barker et al.
10,010,276 B2 7/2018 Al-Ali et al.
10,086,138 B1 10/2018 Novak, Jr.
10,111,591 B2 10/2018 Dyell et al.
D833,624 S 11/2018 DeJong et al.
10,123,729 B2 11/2018 Dyell et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,205,291 B2 2/2019 Scruggs et al.
10,226,187 B2 3/2019 Al-Ali et al.
10,231,657 B2 3/2019 Al-Ali et al.
10,231,670 B2 3/2019 Blank et al.
RE47,353 E 4/2019 Kiani et al.
10,279,247 B2 5/2019 Kiani
10,292,664 B2 5/2019 Al-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,383,520 B2 8/2019 Wojtczuk et al.
10,383,527 B2 8/2019 Al-Ali
10,388,120 B2 8/2019 Muhsin et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,463,340 B2 10/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
10,608,817 B2 3/2020 Haider et al.
D880,477 S 4/2020 Forrest et al.
10,617,302 B2 4/2020 Al-Ali et al.
10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,750,984 B2 8/2020 Pauley et al.
D897,098 S 9/2020 Al-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf et al.
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,154,656 B2 * 10/2021 El-Khatib ............ H04W 76/10
11,185,262 B2 11/2021 Al-Ali et al.
11,191,484 B2 12/2021 Kiani et al.
11,238,133 B1 * 2/2022 Brewer ............... G06Q 10/087
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,382,567 B2 7/2022 O'Brien et al.
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
11,659,023 B2 * 5/2023 Shelton, IV .......... A61B 34/25
709/227
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.

(56) References Cited

U.S. PATENT DOCUMENTS

D999,244 S 9/2023 Indorf et al.
D999,245 S 9/2023 Indorf et al.
D999,246 S 9/2023 Indorf et al.
11,766,198 B2 9/2023 Pauley et al.
11,770,863 B2 * 9/2023 Mandapaka ......... H04B 17/318 709/227
D1,000,975 S 10/2023 Al-Ali et al.
11,803,623 B2 10/2023 Kiani et al.
11,832,940 B2 * 12/2023 Diab .................... A61B 5/7267
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 * 10/2024 Kiani ..................... G16H 40/63
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,362,596 B2 7/2025 Barker et al.
12,383,166 B2 * 8/2025 Desborough ......... A61M 5/003
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
D1,102,622 S 11/2025 Al-Ali et al.
12,478,272 B2 11/2025 Telfort et al.
12,478,293 B1 11/2025 Al-Ali et al.
D1,106,466 S 12/2025 Avendaño et al.
12,495,967 B2 12/2025 Muhsin et al.
12,495,999 B2 12/2025 Al-Ali et al.
12,507,952 B2 12/2025 Al-Ali et al.
12,521,021 B2 1/2026 Al-Ali et al.
12,521,506 B2 1/2026 Yu et al.
12,538,084 B1 1/2026 Telfort et al.
12,539,046 B2 2/2026 Kiani
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0180140 A1 8/2007 Welch et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0122074 A1 * 5/2010 Drucker ................. G16H 40/67 713/168
2010/0138524 A1 * 6/2010 Sobie ...................... H04L 41/12 709/227
2010/0234718 A1 9/2010 Sampath et al.
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0118561 A1 5/2011 Tari et al.
2011/0125866 A1 * 5/2011 Williams ............... G16H 40/67 709/227
2011/0137297 A1 6/2011 Kiani et al.
2011/0172498 A1 7/2011 Olsen et al.
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0041591 A1 2/2013 Lamego
2013/0060147 A1 3/2013 Welch et al.
2013/0096405 A1 4/2013 Garfio
2013/0133036 A1 * 5/2013 Wang ...................... G16Z 99/00 709/217
2013/0160082 A1 * 6/2013 Miller ..................... H04L 67/14 709/227
2013/0296672 A1 11/2013 O'Neil et al.
2013/0345921 A1 12/2013 Al-Ali et al.
2014/0089514 A1 * 3/2014 Messenger ............ H04L 67/141 709/227
2014/0166076 A1 6/2014 Kiani et al.

(56) References Cited

U.S. PATENT DOCUMENTS

2014/0180160 A1 6/2014 Brown et al.
2014/0187973 A1 7/2014 Brown et al.
2014/0275871 A1 9/2014 Lamego et al.
2014/0275872 A1 9/2014 Merritt et al.
2014/0316217 A1 10/2014 Purdon et al.
2014/0316218 A1 10/2014 Purdon et al.
2014/0323897 A1 10/2014 Brown et al.
2014/0323898 A1 10/2014 Purdon et al.
2015/0005600 A1 1/2015 Blank et al.
2015/0011907 A1 1/2015 Purdon et al.
2015/0073241 A1 3/2015 Lamego
2015/0080754 A1 3/2015 Purdon et al.
2015/0099950 A1 4/2015 Al-Ali et al.
2016/0196388 A1 7/2016 Lamego
2016/0367173 A1 12/2016 Dalvi et al.
2017/0024748 A1 1/2017 Haider
2017/0173632 A1 6/2017 Al-Ali
2017/0199985 A1* 7/2017 Mazlish ................ G16H 40/63
2017/0251974 A1 9/2017 Shreim et al.
2017/0325091 A1* 11/2017 Freeman ................ H04W 4/90
2017/0367104 A1* 12/2017 Raisoni ................ H04W 72/12
2018/0043094 A1* 2/2018 Day ...................... G16H 20/17
2018/0137938 A1* 5/2018 Vaddiraju ............ A61B 5/7445
2018/0242926 A1 8/2018 Muhsin et al.
2018/0247712 A1 8/2018 Muhsin et al.
2018/0271451 A1* 9/2018 Chen ..................... G16H 50/20
2019/0239787 A1 8/2019 Pauley et al.
2019/0320906 A1 10/2019 Olsen
2019/0374713 A1 12/2019 Kiani et al.
2020/0060869 A1 2/2020 Telfort et al.
2020/0111552 A1 4/2020 Ahmed
2020/0113435 A1 4/2020 Muhsin
2020/0113488 A1 4/2020 Al-Ali et al.
2020/0113496 A1 4/2020 Scruggs et al.
2020/0113497 A1 4/2020 Triman et al.
2020/0113520 A1 4/2020 Abdul-Hafiz et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0016005 A1* 1/2021 Raskin .................. G16H 10/40
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0177306 A1* 6/2021 Vleugels ............... A61B 5/1112
2021/0178064 A1* 6/2021 Vleugels ............... G16H 20/17
2021/0178067 A1* 6/2021 Grosman .......... A61M 5/14248
2021/0236729 A1* 8/2021 Kiani .................... G16H 40/63
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0377726 A1* 12/2021 Finney .................. H04W 12/71
2021/0386382 A1 12/2021 Olsen et al.
2021/0402110 A1 12/2021 Pauley et al.
2022/0026355 A1 1/2022 Normand et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0151521 A1 5/2022 Krishnamani et al.
2022/0218244 A1 7/2022 Kiani et al.
2022/0232081 A1* 7/2022 Reynier ............... H04L 67/141
2022/0287574 A1 9/2022 Telfort et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Al-Ali
2023/0058342 A1 2/2023 Kiani
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0116371 A1 4/2023 Mills et al.
2023/0135297 A1 5/2023 Kiani et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0226331 A1 7/2023 Kiani et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen
2025/0255764 A1 8/2025 Stead
2025/0278512 A1 9/2025 Koo et al.
2025/0281059 A1 9/2025 Avendano
2025/0288250 A1 9/2025 Al-Ali et al.
2025/0295366 A1 9/2025 Al-Ali et al.
2025/0302426 A1 10/2025 Ha et al.
2025/0311949 A1 10/2025 Al-Ali et al.
2025/0318761 A1 10/2025 Al-Ali et al.
2025/0322950 A1 10/2025 Al-Ali et al.
2025/0323417 A1 10/2025 Rey
2025/0329240 A1 10/2025 Kiani
2025/0344010 A1 11/2025 Al-Ali et al.
2026/0014333 A1 1/2026 Fernkvist et al.

(56) References Cited

U.S. PATENT DOCUMENTS

| | | | |
|---|---|---|---|
| 2026/0014334 | A1 | 1/2026 | Danwihl |
| 2026/0048198 | A1 | 2/2026 | Vo et al. |

FOREIGN PATENT DOCUMENTS

| | | | | |
|---|---|---|---|---|
| WO | WO-2021011697 | A1 * | 1/2021 | ............ A61M 5/142 |
| WO | WO-2021026004 | A1 * | 2/2021 | ......... A61B 5/14532 |
| WO | WO-2021108419 | A1 * | 6/2021 | ........... A61B 5/7275 |

OTHER PUBLICATIONS

Kruchten, Philippe, "Architectural Blueprints-The "4+1" View Model of Software Architecture", Rational Software Corp., Paper published in IEEE Software 12 (6), Nov. 1995, p. 15.

* cited by examiner 2900
2902a
CloudHCP
2902b
CloudManagers
2902c
CloudObservers
Capacity Override
2904
Backup Node
Cloud
HCP or CloudManager
Capacity Override
TLS
2908
Phone
Capacity Override
NFC
STLE
STLE
NFC
2912
SOC Secondary
2910
SOC Primary
2914
Capacity Override
2901
User

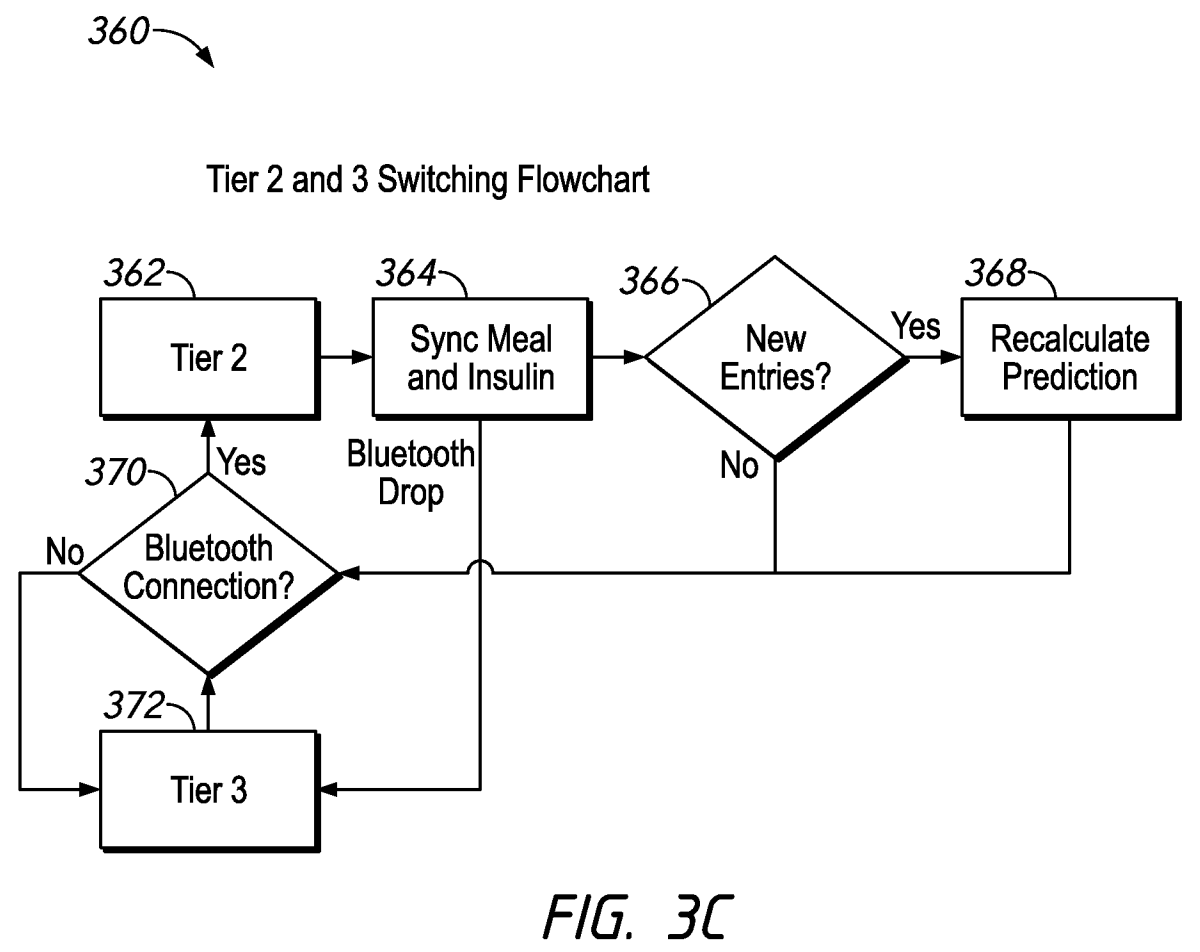

360

Tier 2 and 3 Switching Flowchart

362 Tier 2

364 Sync Meal and Insulin

366 New Entries?

Yes

No

368 Recalculate Prediction

Bluetooth Drop

370 Bluetooth Connection?

Yes

No

372 Tier 3

FIG. 3C

MODEL PREDICTIVE CONTROL IN A CLOSED LOOP CONTROL SYSTEM FOR CONTINUOUS GLUCOSE MONITORING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

The general field of this disclosure is glucose sensing and insulin dosage systems.

BACKGROUND

Diabetes is a chronic disease that impacts many individuals, both adults and children. The management of diabetes may include the measurement of glucose within the interstitial space, including blood and/or interstitial fluid of a patient and administration of insulin to the patient. A closed loop insulin administration system traditionally includes both a sensor to take glucose measurements from the interstitial space and an insulin administration device which administers insulin to the patient based on the glucose measurements. Closed loop insulin administration systems allow individuals impacted by diabetes to go about daily life with much less worry about their insulin or glucose levels and can vastly improve a diabetic's quality of life.

SUMMARY

Closed loop control remains a challenging problem involving the integration of algorithms, optimization, embedded systems, cloud support, mobile apps, $3^{rd}$ party hardware, and potentially complex user interactions. Systems and methods described herein uniquely addresses the above overlapping issues while being as safe as possible and as simple as possible.

In some examples, a glucose control system can include a glucose sensor; an insulin pump; and one or more hardware processors configured to execute instructions to: determine a first connectivity of the hardware processor to a mobile computing device; determine a second connectivity of the mobile computing device to one or more remote hardware processors; and select a control process among a plurality of control processes for operation of the at least one insulin administration system based on the first connectivity and the second connectivity.

In some examples, a method of selecting a control process for an insulin administration system can include: determining a first connection state between at least one glucose control system and at least one mobile computing device; changing a control state of at least one glucose control system to a second control state from a default control state if the first connection state is active; determining a second connection state between the at least one mobile computing device and a cloud computing system; and changing the control state to a third control state if both the first connection state and the second connection state is active.

In some examples, a user authentication system for a glucose control system can include: at least one insulin administration system that can include: a glucose sensor; and an insulin pump; and one or more hardware processors configured to execute instructions to: receive, from a user input device, a request to update a control value associated with the at least one insulin administration system; determine an authorization level associated with a user of the user input device; and allow or deny the update based on the authorization level.

In some examples, a glucose control system can include: a glucose sensor; an insulin pump; and one or more hardware processors configured to execute instructions to: receive a user input, the user input comprising meal intake and insulin intake; determine a first glucose prediction using an empirical model based on the user input; receive a measured glucose value; update the empirical model based on the measured glucose value and the user input; and output an insulin bolus recommendation to the at least one insulin administration system based on the second glucose prediction value.

In some examples, a glucose control system can include: a glucose sensor; an insulin pump; a glucagon administration system; and one or more hardware processors configured to execute instructions to: receive a measured glucose value from the at least one insulin administration system; determine if the measured glucose value falls below a threshold value; determine an orientation of the user; and administer glucagon to a user using the glucagon administration system based on the orientation of the user and a determination that the measured glucose value falls below the threshold value.

BRIEF DESCRIPTION OF THE DRAWINGS

FIG. 2 illustrates an example authentication environment that may be associated with a control system environment.

FIGS. 3C and 3D are flowcharts illustrating an example switching algorithm tiers of a control algorithm.

DETAILED DESCRIPTION

Figure 1A:
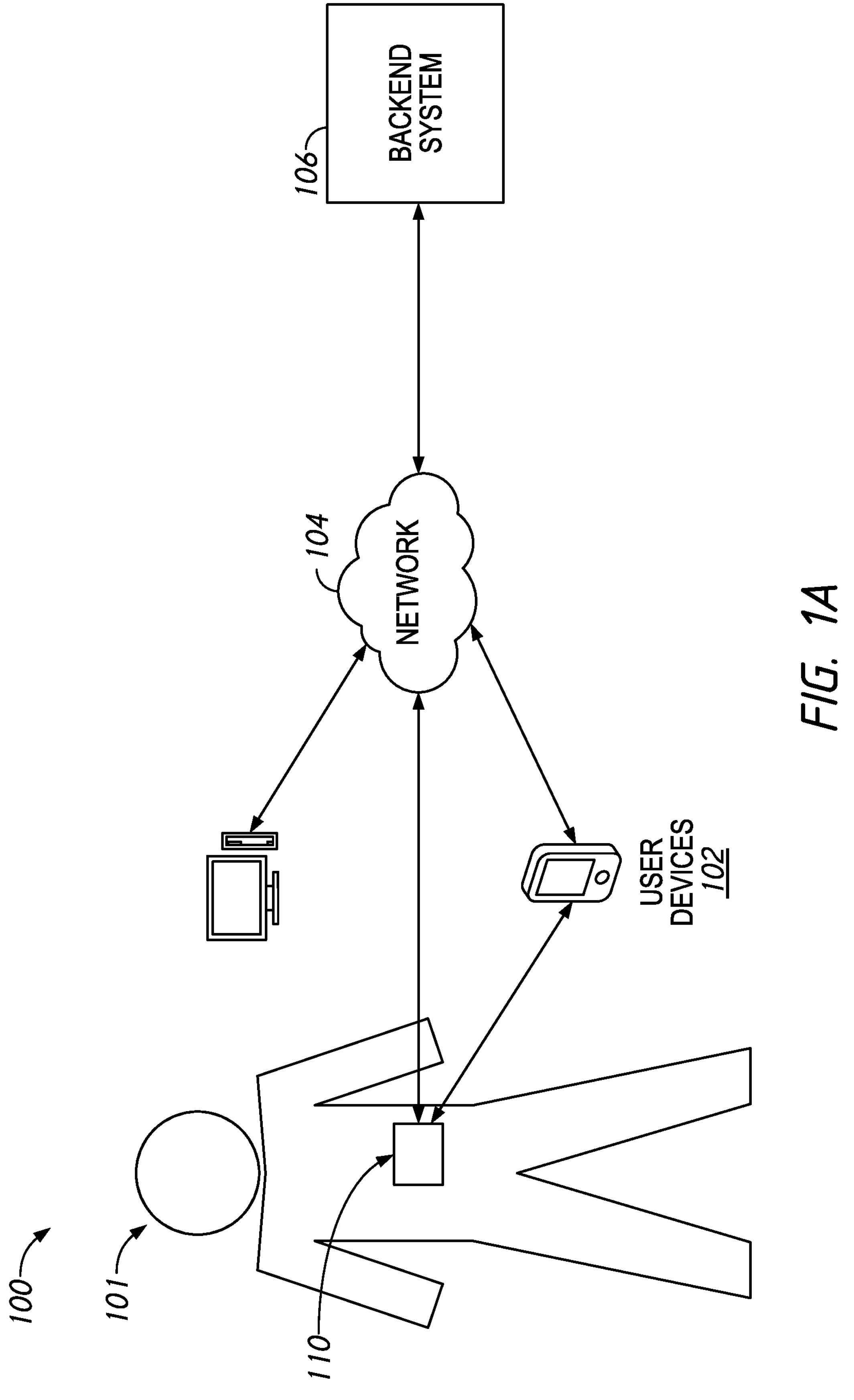
FIG. 1A illustrates an example closed loop environment in which a closed loop system described herein may operate.

Aspects of the disclosure will now be set forth in detail with respect to the figures and various examples. One of skill in the art will appreciate, however, that other configurations of the devices and methods disclosed herein will still fall within the scope of this disclosure even if not described in the same detail. Aspects of various configurations discussed do not limit the scope of the disclosure herein, which is instead defined by the claims following this description.

In a person without diabetes, the body nearly directly measures glucose by the pancreas, liver, and other cells throughout the body. The body then dispenses insulin by the pancreas almost directly into blood. However, in a person who cannot naturally regulate their blood sugar in this way, they may use a medical device control system to control blood sugar, such as a glucose sensing device (for example, a continuous analyte monitor or continuous glucose monitor), insulin delivery device, or a combination device. Ideally, a control system may be configured to control the user's blood sugar through operation of the example medical devices without requiring manual input by a user. This type of control system can be classified as a closed loop control system. Current classes of what are sometimes referred to as closed loop control can fall in two categories: reactive closed loop and hybrid closed loop. Reactive closed loop can be defined as a control system that only changes its stimuli based on observation of analytes. A hybrid closed loop system utilizes user supplied information such as notification of meal or insulin information. However, hybrid closed loop models generally are still highly insufficient to reach normalcy. Closed loop control remains a challenging problem involving the integration of algorithms, optimization, embedded systems, cloud support, mobile apps, 3rd party hardware, and potentially complex user interactions.

One example complexity of a closed loop control system involve delays and other errors. For example, in a medical device control system, glucose is measured interstitially with approximately a 15-minute delay and is dispensed interstitially with approximately a 15 minute delay. Thus, a good model of the body to enable forward accounting of these delays is needed. Described herein are aspects of a control system that can help account for these delays and other errors.

In some examples, a control system may recognize patterns in individuals' physiology and reaction to stimuli as well as user behavior and insulin response to provide a better control algorithm. This pattern recognition may include user-specific observations, including individual and population related (or long-term) patterns and model-based (or short-term) patterns.

In some examples, a time in range (TIR) may be greater than 70% when using the control system while having a cloud connection. In some examples, under a cloud connection, closed loop may remain on greater than 90% of the time without being forced into manual mode by a condition, such as a probe-off event. In some examples, a TIR may be greater than 60% while having only an app or local device connection. In some examples, under only a local device connection, closed loop may remain on greater than 90% of the time without being forced into manual mode by, a condition, such as a probe-off event. In some examples, a TIR may be greater than 50% while using only the embedded device. In some examples, using only the embedded device, closed loop may remain on greater than 90% of the time without being forced into manual mode by a condition, such as a probe-off event. In some examples, a TIR performance and user safety may be improved by a cloud connection.

In some examples, the control system may suspend insulin on low detected absolute or derivative CGM glucose or model prediction value configurable thresholds. In some examples, the control system may interact with an application, such as to notify an application or mobile computing device running an application regarding a suspension of insulin or other condition change of a glucose control system.

In some examples, a control system may have a glucose set point or target range mode. The set point or target range may be based on user context. In some examples, the set point or target range may be temporary in nature and detected.

In some examples, at least one embedded closed loop control algorithm may be configured to function independently of one or more of an application, mobile device, or cloud-based processor. For example, an embedded closed loop control algorithm may be configured to function independently of a cloud-based processor but utilize an application running on a mobile device for dosing verification and meal entry. In another example, an embedded closed loop control system algorithm may be configured to function independently of both a cloud-based processor and an application running on a mobile device.

In some examples, an arbitrator algorithm may be configured to determine the best insulin dose for a user at a point in time based off of some combination of data, including but not limited to embedded data (such as data on a CGM or insulin pump device), phone data, cloud data, algorithms, meta information, heuristic information of a user, and other information.

In some examples, a control system may be configured to incorporate insulin injections associated with an insulin pump. In some examples, a control system may be configured to incorporate external insulin injections, such as syringe (muscle or ISF), patch, and inhaled from various vendors.

In some examples, a user's personal insulin sensitivity shall be assessed after oral glucose tolerance test (OGTT) like meals are consumed and logged. An OGTT like meal may include, for example, a meal with a certain number of carbohydrates or high glycemic index foods. In some examples, records of the insulin type may be retained for possible future calibrations of aspects of the control system with that insulin type.

In some examples, a control system may utilize electronic health records (EHR) to improve personalization, such as around sparse variables of interest including but not limited to: HbA1C, fasting glucose test, existing disease progression, or other blood works considered gold standards.

In some examples, a control system may use lipid information to make mealtime corrections or determine meal time confidences.

In some examples, a control system may dynamically re-estimate quantity of meal quantities based on Continuous Analyte Monitor (CAM) measurements.

In some examples, a control system may use a rate of appearance and food quantity to retrospectively modify a food particle size in order to properly account for large CGM oscillations (for example, 30-minute time periods). In some examples, a control system may use fine sampling rates (for example, 1-minute measurements) to assess the personal delay time of users pylorus when CGM short oscillations occur (for example, in a 5 minute time frame) due to high nutrient levels. Additionally or alternatively, the trigger threshold for opening and closing the pylorus shall be assessed.

In some examples, a user body temperature may be measured to provide alarms related to a user condition, such as whether the user is having a fever or not.

In some examples, a body orientation may be monitored based on device orientation. A body orientation may include, for example, if a user is on their back, belly, or butt. In some examples, a control system may allow a user-engaged calibration for a body orientation. In some examples, a control system may use a body placement to historically and personally analyze insulin absorptivity rate.

In some examples, a control system may include an SIQ system that takes into account electrical instability, and/or known sensor-body responses.

In some examples, a control system may monitor, in cloud, confidence that the system is likely in full use. For example, the control system may monitor that the user is supplying all required information, including, but not limited to meal information, insulin injections, and activity.

In some examples, a control system may monitor that a CGM or CAM output(s) stay contained in at least one state of a model, such as a glucose-insulin-lipid meal model (GLIMM). In some examples, if the output(s) deviate more than a threshold amount, a notification may be sent to app.

In some examples, a control system may monitor internal MPC states with simple thresholds to prevent erroneous dosing. In some examples, a control system may monitor outbound insulin dosing with simple rules to act as a sanity check. Insulin on board may be monitored with simple rules to prevent overdosing from the app. In some examples, a control system may monitor personalized insulin dosing based on heuristic dosing of a user and compare it with current dosing to prevent overdosing.

In some examples, a control system may determine physical activity confidence via one or more sensors and/or input data, such as accelerometer, gyroscope, pulse rate monitor, SpO2 monitor, GPS, time of day, whole body model states.

In some examples, a control system may generate an alarm on oxygen lows that may indicate hypoglycemic or compression related low events or independently bad events such as opioid overdoes with the SpO2 and use the SpO2 to detect sleep apnea or other sleep disorders.

In some examples, a control system may monitor diffuse reflectance SpO2 to estimate insulin metabolism at a measurement site to assess oxygen consumption by GOx in a glucose sensing device.

In some examples, a control system may maintain a historically safe personalized user configuration in order to provide a safe operating mode for a glucose sensing device.

In some examples, a control system may generate a cloud-based confidence in expected patterns for insulin bolus, based on one or parameters, including but not limited to exercise behavior, food bolus, phone GPS location, time of day, sleep status, pulse rate, and SpO2.

In some examples, a control system may predict at what time an insulin reservoir in a glucose sensing device and/or insulin pump will go to zero or have an empty state. In some examples, a control system may use a threshold to determine the time at which a new device should be put on the body (for example, because a reservoir is in an empty state) and this information can be communicated to the user through an application on a mobile device or by an alert on the glucose sensing device and/or insulin pump itself.

In some examples, a control system may determine an effectiveness of insulin for a user based on some combination of temperatures, time, and dose accordingly for insulin reservoir(s), such as reservoirs in one or more of a primary and secondary glucose sensing device.

In some examples, a control system may detect when a user is moving towards hypo or hyperglycemia. In some examples, a control system may test into the future as far as a few hours.

A. Control System Components

A closed loop system may consist of a combination of users and hardware. FIG. 1A illustrates an example closed loop environment 100 in which a closed loop system described herein may operate. For example, a closed loop environment 100 may include a user 101, one or more sensor devices 110, one or more user devices 102, a network 104, and a backend system 106.

A user 101 may interact with the one or more sensor devices 110 directly or through one or more user devices 102. The one or more user devices 102 may include a smart device, such as a smart watch, smart phone, tablet, computer, the like or a combination thereof. It should be noted that a user's mobile device, such as a smart phone, may or may not be considered a permanent communication line. In some examples, a user's mobile device, such as a phone, may not be required by the embedded closed loop system to keep the user in tight glycemic control.

In some examples, the one or more user devices 102 may communicate with a sensor device 110 and/or a backend system 106 through a network 104. For example, a user device 102 may receive data from a user 101, such as a time and composition of a user intake of food. The user device 102 may communicate the data, through the network, to the backend system 106. The backend system 106 may then transmit information based on the received data to the user device 102. In some examples, a user device 102 may directly communicate with a sensor device 110 through wires or wirelessly. In some examples, a wireless mode of communication can include, but is not limited to, Wi-Fi, NFC or Bluetooth connection.

Figures 1, 1B, 1C, 2:
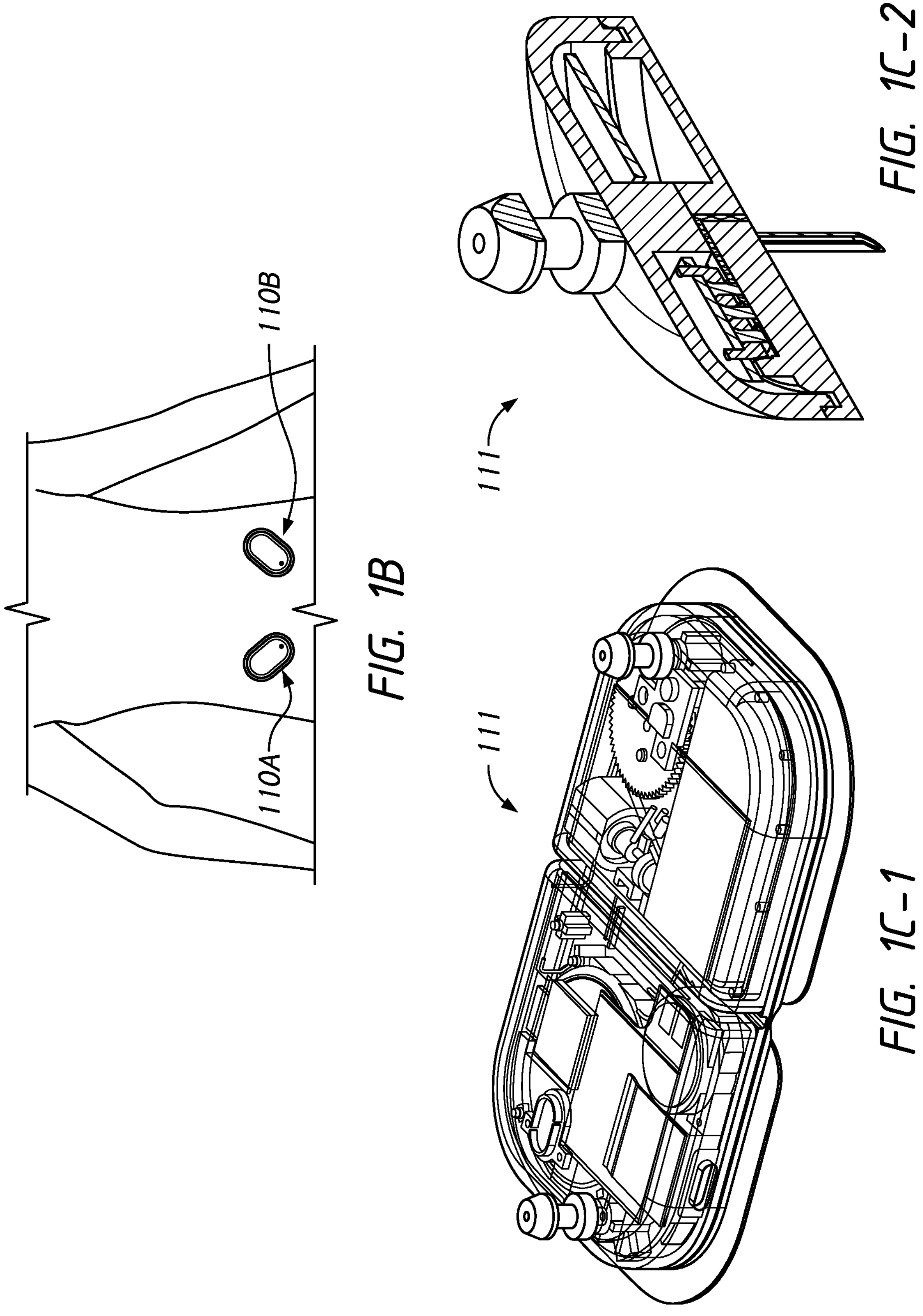
FIGS. 1B and 1C-1 and 1C-2 illustrates example hardware components that may be part of a closed loop environment.

In some examples, one or more components of a closed loop system may include at least one medical control device 110. A medical control device 110 may be configured to upload and/or receive data through the user device 102 or the network 104. As illustrated in FIG. 1B, in some examples, one or more hardware components may include a plurality of medical control devices 110A, 110B, such one or more of a continuous glucose monitor, continuous analyte monitor, other analyte monitor, insulin pump, combination device, or the like. In some examples, medical control devices 110 may include a primary sensor device 110A and a secondary sensor device 110B. Advantageously, this may allow for redundancy and staggered active use of glucose sensors so as to allow for at least one glucose sensor 110 to be active and calibrated at any given time during use. In some examples, one or more control devices 110A, 110B may include a single sensor device and an insulin pump. In some examples, one or more sensor devices 110A, 110B may include a combined glucose sensor and insulin dosage system 111, such as illustrated in FIGS. 1C-1 and 1C-2, illustrating a perspective see-through view and cross section view respectively, and as described in application Ser. No. 17/161,528, filed Jan. 28, 2021, titled "REDUDANT STAGGERED GLUCOSE SENSOR DISEASE MANAGEMENT SYSTEM," which is incorporated by reference herein.

Figure 1D:
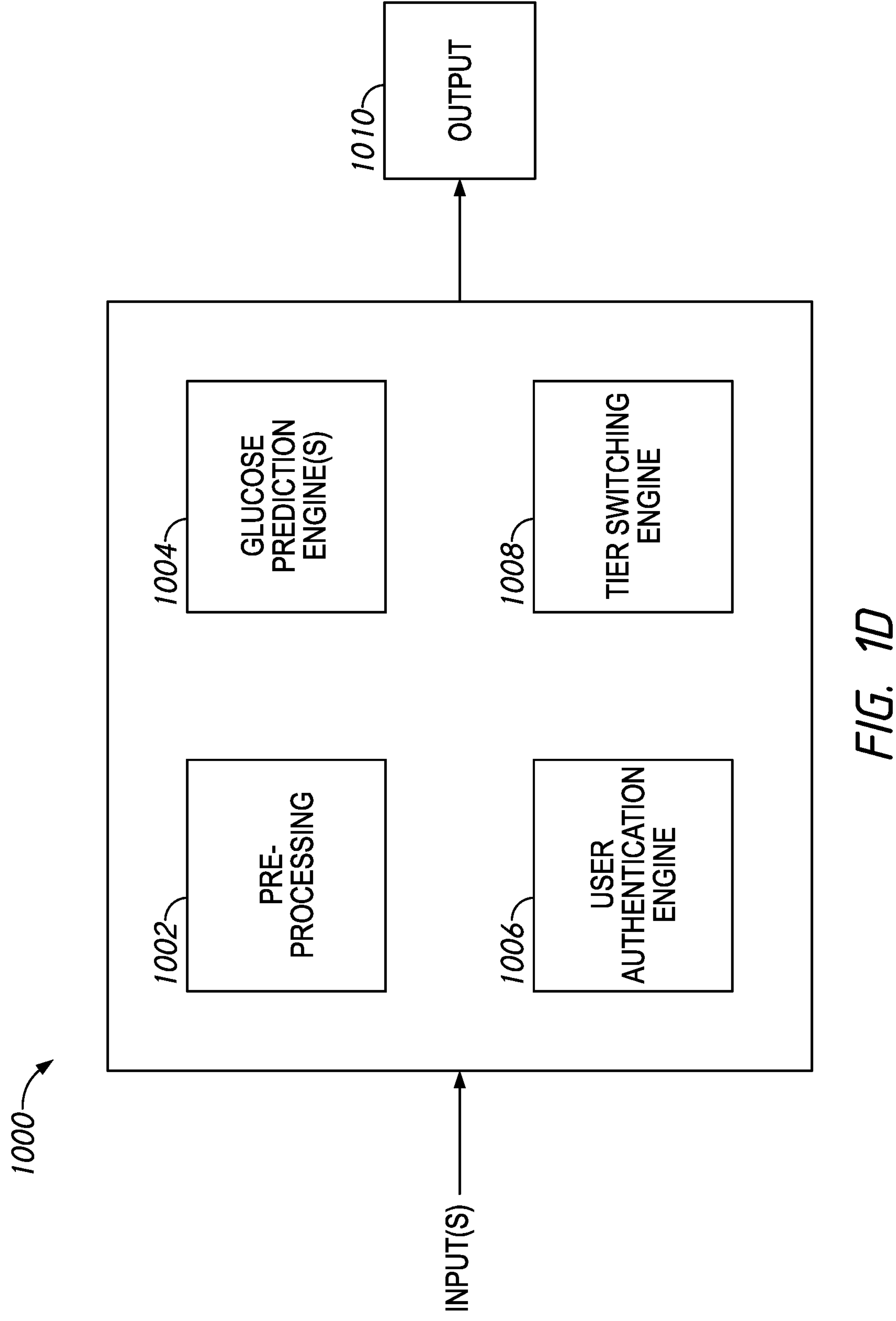
FIG. 1D illustrates an example controller that may be configured to process one or more inputs associated with a closed loop environment.
Figure 2:
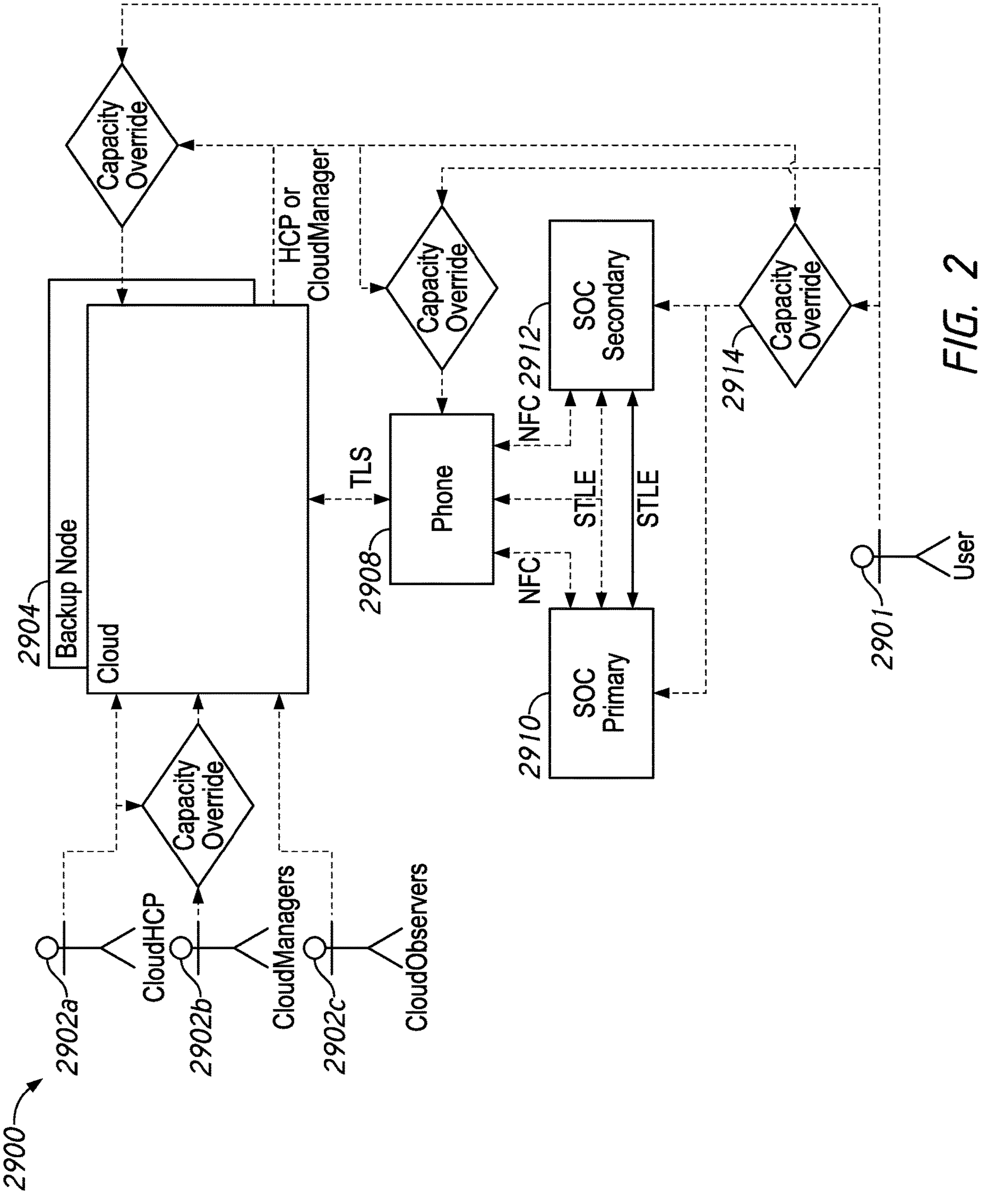

FIG. 1D illustrates an example controller 1000 that may be configured to process one or more inputs associated with a closed loop environment 100 to provide outputs 1010 to one or more of a medical control device, such as described above, user device, or other computing device. In some examples, the one or more inputs may include user input data, device data, medical record data, or other data related to the user or devices in the closed loop control environment 100. In some examples, an output 1010 can include a user device configured to display information associated with a user's glucose control or other health state. In some examples, an output 1010 can include one or more devices in a closed loop control environment 100, including but not limited to, a backend system, user device, glucose sensing device, insulin delivery device, combination sensing and insulin delivery device, the like or a combination thereof.

In some examples, a controller 1000 may include a plurality of engines. For examples, a controller 1000 may include a pre-processing engine 1002, one or more glucose prediction engines 1004, a user authentication engine 1006, a tier switching engine, or other engine.

A pre-processing engine 1002 may include one or more processes for processing or analyzing inputs to the controller 1000 for further processing by the controller. For example, a pre-processing engine may include data cleaning, selection, normalization, transformation, feature extraction, reduction, other data processing, the like, or a combination thereof.

One or more glucose prediction engines 1004 may include one or more processes for modeling or predicting a glucose or other physiological response of a user based on one or more parameters and/or inputs for a physiological model. In some examples, a glucose prediction engine 1004 may include model predictive control (MPC) using a physiological model, such as a Glucose Insulin Meal Model (GIMM) or the like. In some examples, a glucose prediction engine 1004 may include a less computationally expensive glucose prediction algorithm, such as referenced in lower tiered algorithms referenced below in relation to the tier switching engine 1008.

A user authentication engine 1006 may include one or more processes for authenticating a user for access to one or more aspects of a control system environment 100. For example, a user authentication engine 1006 may identify a user and provide access based on the user identity and an associated authorization level to access, edit, view, or otherwise interact with information associated with one or more of the devices in the control system environment 100, with the user or a user physiological condition, other information associated with the user (for example, a medical record), or other aspects of a control system environment 100.

A tier switching engine 1008 may include one or more control algorithm selection processes. For example, a tier switching engine 1008 may include decision logic associated with selecting a glucose prediction engine 1004 to use in controlling aspects of a control system environment, including but not limited to, glucose sampling times and insulin injection times.

A controller 1000 may use other engines or processes in addition or in the alternative to those described herein in order to analyze information related to the control system environment 100 and output data, such as a control signal to one or more devices in a control system environment 100 or a visual display on a mobile device application.

B. Example User Authentication Engine

A user is the culmination of major concern in a closed loop system and as such, if mentally and physically able should be granted access to all necessary subsystems in a software architecture. Should a user have impaired capacity or education, an architecture may limit authority of the user to make potentially life threatening choices. In some examples, a software architecture may include higher levels of user authority for final judgement on system behavior and limits on system operation. Levels of authority and limits on system operation may be dependent on specific user conditions. As referenced above, a controller may utilize a user authentication engine 1006 to facilitate access to aspects of a control system environment 100 based on levels of authority and/or identify of a user.

In some examples, variables that impact closed loop behavior and that may be accessed or modified at different levels of permission can include, but are not limited to level of author, level of system access, and encrypted binary BLOBs (or binary large objects), such as: variable name, variable notation, units of variable, model type (such as a patient model or MPC model), whether the variable is linearized or not, read and write ability of each variable (for example, is the variable something only being transported, is it something the user can configure, or is there an algorithm in that domain that can take a decision to change a variable), maximum upper limits (UL) of insulin or other values and minimum lower limits (LL) of insulin or other values if applicable (for example, a user may only set the insulin sensitivity from 0.75 to 1.25 in a mobile application, but on device or in the cloud, the range can be set from 0.5 to 2.0), safe mode value or function (such as personalization function for an MPC model), and starting mode value or function. In some examples, values of some variables may be fixed or read only. In some examples, values of variables may change as a result of user interaction with the system, outcomes of calculations, or other input or output of the control system.

In some examples, different components and users of a control system may have different access levels or authorizations to read, write, or edit different variables related to the control system, such as described above. For example, components may include a cloud based device, a user device (such as a mobile device or other computing device), primary sensor device, secondary sensor device. User(s) may include a patient using the sensor device(s), a health care provider, a manager, an observer, or other user. In some examples, a user may interact with the control system using a user device directly or indirectly connected with a sensor device, such as through an application on a mobile device. For example, a user may input meal information into an application in the mobile device, which may then communicate information associated with the input to the sensor device or to a cloud based device. In some examples, a user may interact with the control system through the cloud based device. For example, a user may read or access use information of the sensor device through a web based portal on a user's mobile device or other computing device.

In some examples, different users may have set authorization settings. For example, a patient may be given full or partial access to control necessary aspects of the control system based on contextual information associated with the user related to mental capacity, education, physical capacity, the like or a combination hereof. For example, an underage user may be granted partial access until they reach a certain age or reach a satisfactory competency in the use of one or more components of the control system or in managing their condition. The access level may be set by a managing user, health care provider, or other user. For example, a managing user, healthcare provider, or other user may have access to more than a full patient access in order to manage or override one or more aspects of the control system, such as to set user access levels.

FIG. 2 illustrates an example authentication environment 2900 that may be associated with a control system environment 100, such as illustrated in FIG. 1A. For example, an authentication environment 2900 may include one or more users 2902*a*, 2902*b*, 2902*c* other than the patient user 2901. The users may have different access or authentication levels for accessing user data that may be stored on a backend system 2904 or in the cloud. For example, a healthcare provider user 2902*a* and manager 2902*b* may have override permissions. Override permissions may include the ability to interact with a user's primary device 2910 and/or secondary device 2912 by communicating instructions to a backend system 2904 that may in turn communicate instructions to a user's mobile device 2908 or directly to the devices 2910, 2912. The mobile device 2908 of a user 2901 may then communicate instructions to the primary device 2910 and/or secondary device 2912 that may be applied to a user 2901. In other examples, an observer user 2902*c* may have observer only permissions that do not enable communication of instructions or override to a user's devices. In some examples, a user 2901 may have either override or observer only permissions. A user 2901 may be granted override or observer only permissions based on factors, such as user age. For example, a child user may be given observer only permissions and an adult user may be given override permissions. Permissions may be assigned by a manager user 2902*b*, user 2901, healthcare provider user 2902*a*, or automatically based on determined factors.

C. Example Tier Switching Engine

The interaction between different hardware devices and users during different levels of connectivity between devices can cause complications when running a closed loop system. For example, as described above with reference to FIGS. 1A-1C, a closed loop system 100 may both need access to external computational resources to perform needed and computationally heavy calculations and allow a glucose monitoring device to run locally without dependence on an external device in order to provide a reasonable amount of consistency for control to keep a user within range. A break in the line of communication between a device and an external hardware processor may thus result in added delays, errors, and other difficulties in use of a glucose monitoring device. In some examples, a system software architecture described herein may be structured to address potential issues caused by disruptions in communication between components of a closed loop system 100.

In some examples, a controller 1000 may use a multi-tiered algorithm or a multi-tiered glucose prediction engine 1004 to handle variables that impact closed loop behavior and/or manage access to changes to the variables. As noted above, different components may communicate with each other. In some examples, communicated data may include instructions relating to future glucose values, predictions and measured glucose, meal intake, or other user input data. In some examples, different components may be configured to analyze or handle different levels of information and/or apply different models based on connectivity. For example, a sensor device alone may be unable to perform complex predictive calculations to enable the most accurate glucose predictions for insulin delivery due to issues with computational resources or inability to directly receive relevant information, such as user input data related to meal intake. Accordingly, a sensor device may communicate with an external hardware processor, such as a mobile device, or a cloud based processor, to send or receive instructions relating to insulin delivery, glucose predictions, measured glucose values, the like or a combination thereof. Thus, in a fully connected system, multiple connected devices may work together to provide a more accurate closed loop system for glucose control. However, if connectivity between a sensor device, user's mobile device, and/or cloud device is broken at some level, dangerous errors relating to glucose control may occur without proper handling by the control system. In some examples described herein a tiered control system to handle variables relating to the control system and improve glucose control. In some examples, due to the limited performance capabilities and memory constraints of microprocessors in one or more control system components, a three-tiered algorithm can be implemented to allow for the best glycemic control for the user given different levels of connectivity.

In some examples, different tiers may correlate to different levels of connectivity. For example, tier 1 may correlate to a full or near-full connectivity scenario, tier 2 may correlate to a medium level of connectivity, and tier 3 may correlate to a low level of connectivity. Tier 1 may run on the cloud and uses MPC and can only be computed if there is connection to between the sensor device and the user device and connection to the cloud. Tier 2 runs on the device and uses the user entered meal or insulin from the phone if there is connection to the user's device. Tier 3 runs on the device and does not require any connection to function.

Tier 1 is a best-case scenario, where the user has the sensor device(s), the user device connected with the sensor device(s) (for example, within Bluetooth range), and cloud connectivity (for example, via Wi-Fi or cellular network connection). Since there is virtually unlimited processing and memory in the cloud, more computationally expensive algorithms, such as MPC (Model Predictive Control), can utilize a physiological model of the user to predict future glucose values and determine the optimal sequence of stimuli necessary to achieve a desired outcome. The cloud algorithm will take past and present observations to generate a model that simulates glucose and insulin transfer between different organs or compartments of the body. Thus, the cloud algorithm can foresee the effect of meal intake and insulin injection on the plasma and interstitial fluid glucose at future points in time. In this way, the algorithm can recommend a set of insulin doses in the present and future to compensate for glucose excursions due to meals and other effects.

Tier 2 is a middle-case scenario, where the user has the sensor device(s) and the user device connected with the sensor device(s) (for example, within Bluetooth range), but the cloud is unavailable. The smart phone may not run any major algorithm code because the code running on the phone cannot be ensured to be secure. The smart phone still allows the user to interact with a medical control device, by allowing user input to specify when a meal will occur with the number of carbohydrates or other nutritional information. This allows the algorithm to correctly bolus the necessary amount of insulin to counteract the effect of carbohydrates to keep the user in the target range. The user may also set temporary basal effects in anticipation of future exercise, sleep, stress, caffeine, etc., which will affect the user's insulin sensitivity and requirements.

Tier 3 is the most conservative scenario, where the user has the sensor device(s), but does not have the user device connected and does not have cloud connection. In a tier 2 state, the algorithm will deliver insulin reactively to recent glucose measurements to keep the user in the target range. The model for the prediction is a deterministic one, which models the average pharmacokinetics and pharmacodynamics of insulin injection and diffusion in the body. The algorithm will be conservative in the dosage of insulin to minimize the number of hypoglycemic events.

A control system may not be continuously in a single tier (1, 2, or 3) of closed loop coverage. As connectivity changes, the algorithm chosen to dose insulin safely for that time period will dynamically change. In some examples, the tier 3 algorithm may also supply a prediction and planned stimuli of how they user may respond given only tier 1 or tier 2 algorithmic control.

As an example, a user may have just received the 30 minute time prediction from the tier 3 algorithm. This prediction and planned stimuli looking forward in time will be saved in the embedded software of the device. At the next time step, connectivity may cease to both the cloud and the user device. The sensor device may choose to hybridize its tier 1 basal closed loop algorithm with the high confidence 30 minute extrapolation of the tier 3 algorithm over the next few measurements. This would be valid so long as the device is not notified of any new environmental stimuli such as an insulin bolus or the device continues to see the CGM outputs course be very similar to the tier 3's 30 minute extrapolation. Should the device see a deviation from the tier 3 extrapolation, it may resume entirely to tier 1 algorithmic control and comparisons to the prediction and planned stimuli therein. Should the device see a deviation from the tier 1 extrapolation it may suspend all insulin dosing and even raise an alarm.

As another example, a user may have just received the 30 minute time prediction from the tier 3 algorithm. This prediction and planned stimuli looking forward in time will be saved in the embedded software of the device. At the next time step connectivity may cease to the cloud. The sensor device may choose to hybridize its tier 2 hybrid closed loop algorithm with the high confidence 30 minute extrapolation of the tier 3 algorithm over the next few measurements. This, of course, would be valid only so long as the device is not notified of any new environmental stimuli such as an insulin bolus, food bolus, or the device continues to see the CGM outputs course be very similar to the tier 3's 30 minute extrapolation. Should the device see a deviation from the tier 3 extrapolation it may resume entirely to tier 2 algorithmic control and comparisons to the prediction and planned stimuli therein. Should the device see a deviation from the tier 2 extrapolation it may suspend all insulin dosing and even raise an alarm.

Figure 3A:
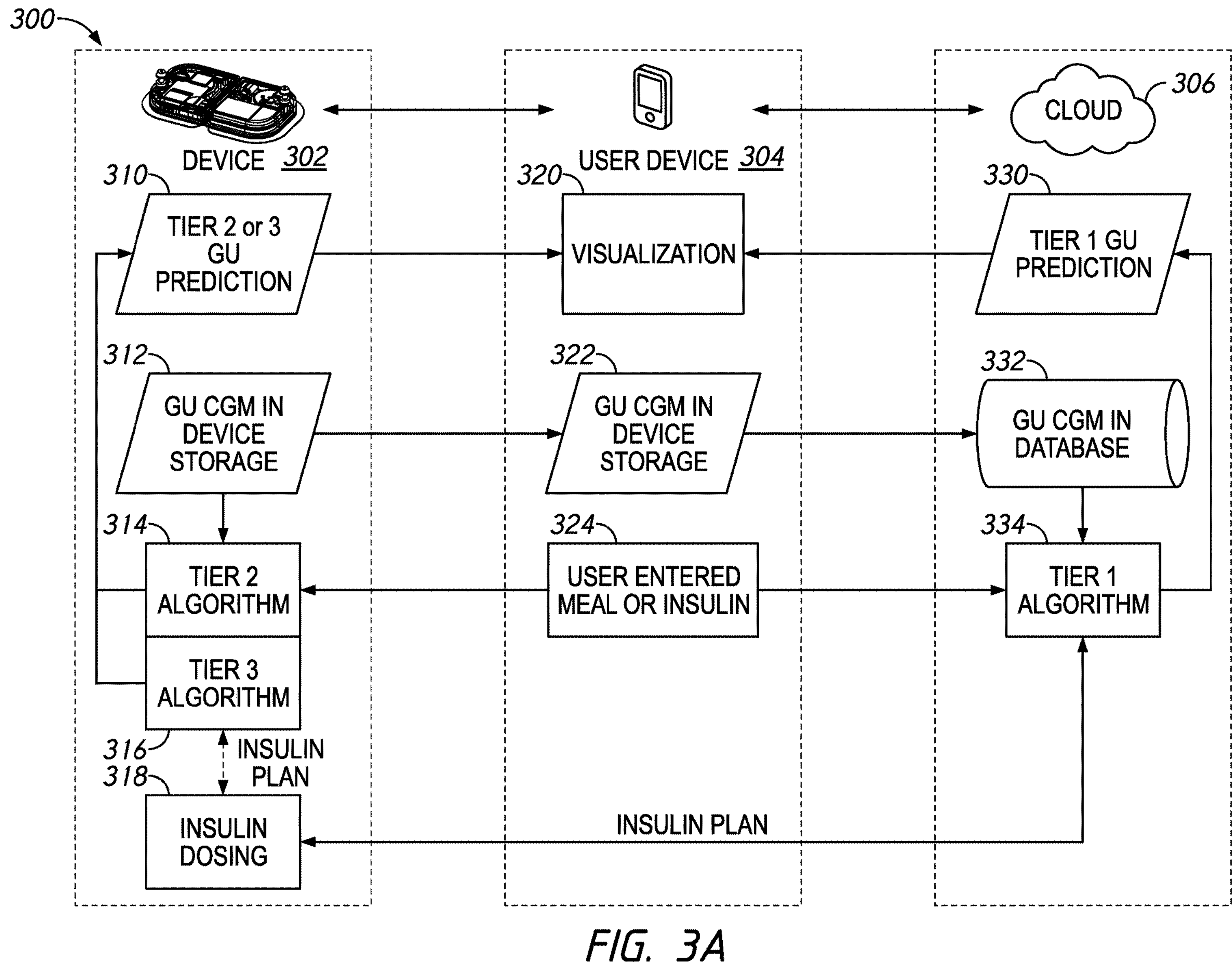
FIG. 3A illustrates an example tier switching environment.

FIG. 3A illustrates an example tier switching environment 300. A tier switching environment 300 may include one or more of a sensor device 302, one or more of a user device 304, and the cloud 306. Devices in the tier switching environment 300 may be configured to communicate with other devices in the tier switching environment 300. For example, a sensor device 302 may communicate with a user device 304 using a bluetooth connection, WiFi, NFC, or other connection technique. In another example, a user device 304 may communicate with one or more cloud based processors 306 using a WiFi, cellular, or other connection technique.

In some examples, a sensor device 302 may measure one or more physiological parameters, including, but not limited to, glucose associated with a user 101. Glucose or other physiological parametesr 312 may be stored on device 302. If a user device 304 and sensor device 302 are in communication, the sensor device 302 may transmit the glucose or other physiological parameter, history of insulin dosing 318, tier 2 or 3 glucose prediction, or other values to a user device 304 and stored on the user device 304 storage 322. The user device 304 may transmit user entered values 324, such as meal or insulin to the sensor device 302. If a user device 304 is connected to the cloud 306, a user device 304 may transmit the glucose or other physiological parameter, user entered values 324, history of insulin dosing 318, or other values to the cloud 306 and stored in a database 334 on the cloud 306. A cloud 306 may transmit a tier 1 glucose prediction 330 to a user device or other values to a user device 306 or sensor device 302.

A tier 1 algorithm 334 on the cloud 306 may generate a tier 1 prediction 330 based on input information that may include, but is not limited to, the glucose or other physiological parameter and/or an insulin plan or intake. The tier 1 prediction 330 may include a glucose prediction associated with a particular or approximate time in range, error rate, or other parameter indicative of quality or accuracy of the glucose prediction. In order for the Tier 1 algorithm 334 to produce a Tier 1 glucose prediction 330, the prediction algorithm 334 may use the glucose measurement 312 that is calculated on the sensor device 302. This measurement 312 may be passed through the user device 304 to the cloud 306 and stored in the patient database 332. The Tier 1 algorithm 334 may use the CGM glucose measurement 312 and calculate future prediction 330 of glucose for a visualization 320. It also may create an insulin plan for the future, which is sent through the user device 304 to the sensor device 302. The sensor device 302 may decide how to incorporate this insulin plan into the actual insulin that is dosed to the subject. For example, it can be blended with Tier 2 and 3 algorithms in the event of cloud connection drops. Tier 1 and 2 algorithms both may use the user entered meal or insulin so that they can dose insulin accordingly to compensate for the expected rise in glucose. Therefore, the user device 304 may be configured to supply this information to the sensor device 302 and the cloud 306.

Figure 3B:
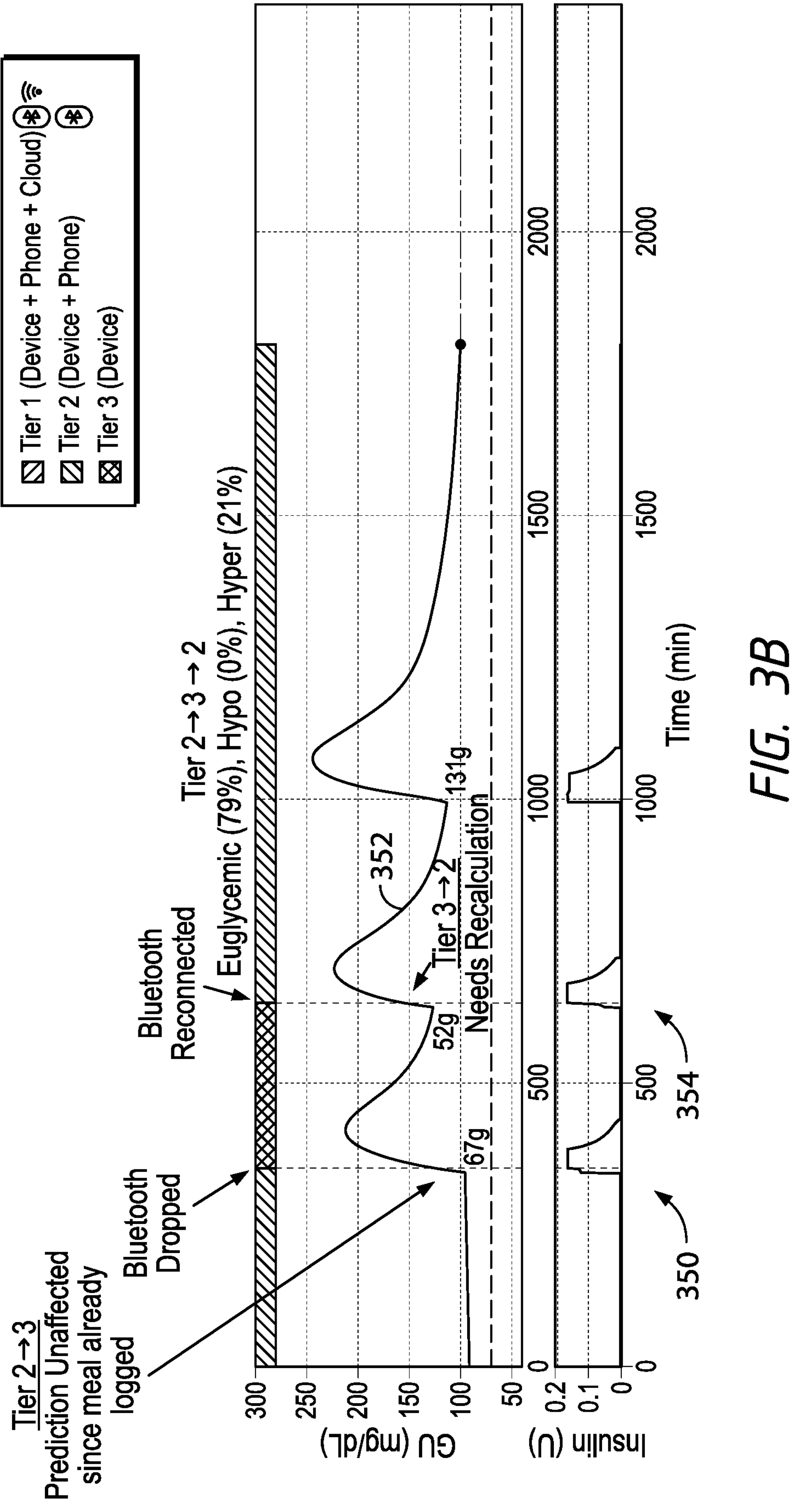
FIG. 3B illustrates an example simulation of a glucose prediction and insulin dosing during a dropped connection between a sensor device and a user device.

FIG. 3B illustrates an example simulation of a glucose prediction and insulin dosing during a dropped connection between a sensor device 302 and user device 304. In the example simulation, the control system begins in Tier 2 due to a lack of connection to the cloud 306. A food event of 67 g of carbs is logged and is incorporated in the Tier 2 calculation just before a connection to the user device 304 is dropped at event 350. However, since the meal was already logged, the glucose prediction 352 is unaffected because the meal was already logged. Even though the system is running in Tier 3, it is effectively equivalent to Tier 2. Another food event occurs just before reconnection to a user device 304. At the next food event, the user logs 52 g of carbs. However, since there is no connection to the user device 304, the device cannot use this information. When Bluetooth connection is re-established at event 354, the algorithm retroactively updates past states of the algorithm to reflect the meal that was logged in the past. Then, the model propagates forward from the time when the meal was logged until it reaches the current point in time so that the glucose prediction and insulin dosing algorithm can be calculated.

FIG. 3C illustrates an example flowchart illustrating an example switching algorithm 360 between Tiers 2 and 3. The tier switching system 360 starts in Tier 3 at block 372. The tier switching system 260 may determine if a connection to a user device 304 is established at a block 370. If connection to a user device 304 is established, the system switches to Tier 2 at block 362. At this point, the user device 304 will sync user entered meal and insulin with the sensor device 302 at block 364. If at any time, the connection is dropped, the system reverts back to Tier 3 at block 372. The tier switching system may determine if there are any new user input entries at block 366. If there are no new meal or insulin entries from the last sync, the tier switching algorithm does not to need update. However, if there are new meal or insulin events, then the prediction will be recalculated at block 368.

Figure 3D:
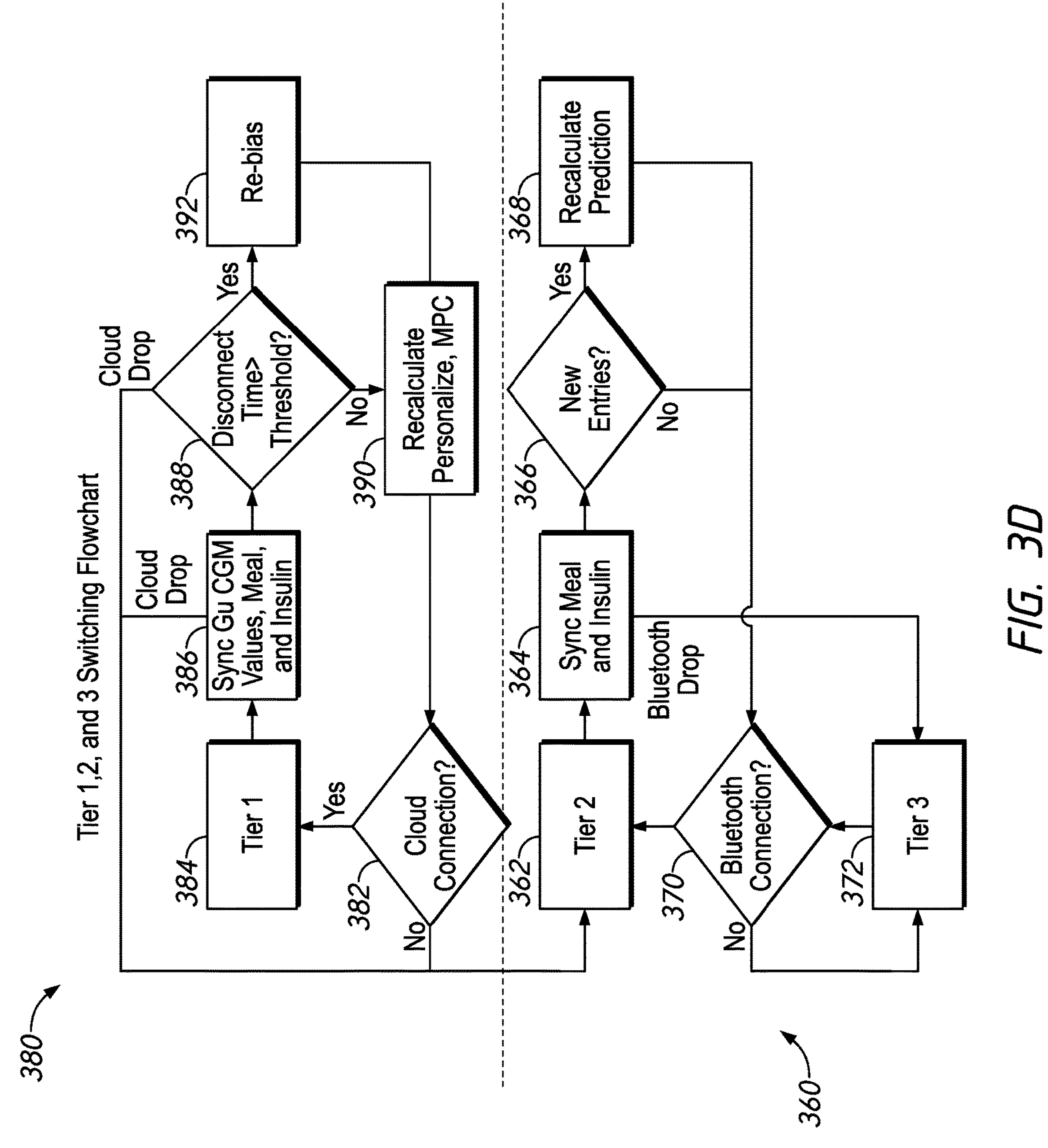

FIG. 3D is an example flowchart illustrating an example switching algorithm 380 for switching between tiers 1, 2, and 3. In the illustrated example, the bottom half of the flowchart is the same or equivalent to the Tier 2 and 3 switching algorithm 360 illustrated and described with reference to FIG. 3C. Starting from Tier 2 at block 362, a tier switching system 380 may determine if a cloud connection has been established at a block 382. If cloud connection is established, then the system switches to Tier 1 at block 384. The user device 304 may then sync the glucose CGM values and user entered meal and insulin values with the cloud at block 386. If at any time cloud connection is dropped, the system reverts to Tier 2 at block 362. The system 380 may determine if a threshold time has elapsed sin the last tier 1 or cloud connection at block 388. If too much time has elapsed since the last Tier 1 connection, then the model may be re-biased to a glucose CGM value in the past at a block 390 and the glucose prediction must be recalculated at a block 392. In some examples, personalization may be used to better tune the model to the newly synced glucose values. Lastly, MPC may be called to calculate the insulin dosing plan.

Figure 4A:
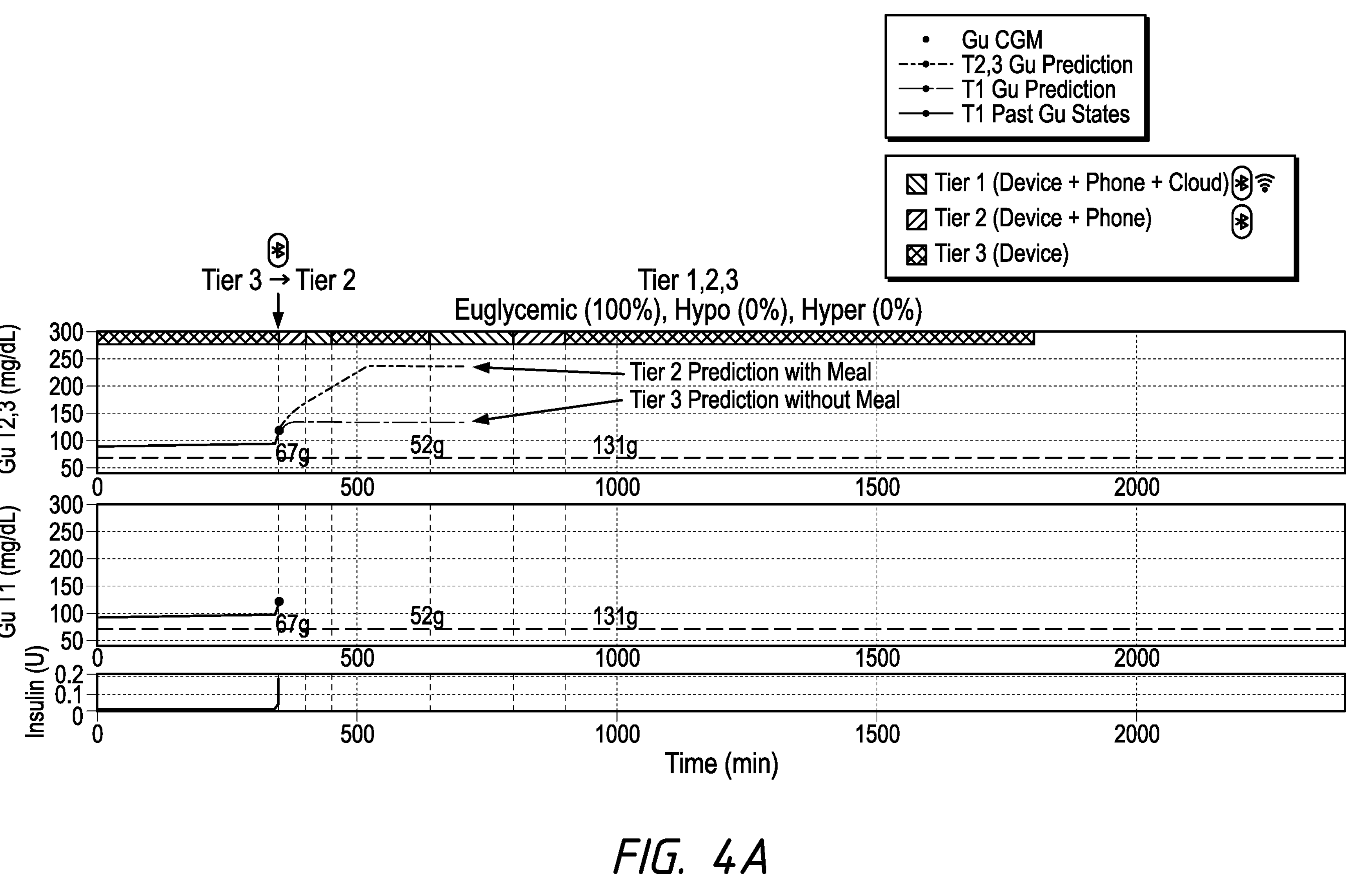
FIGS. 4A-4D illustrate example simulations of switching to different tiers using a tier switching algorithm.
Figure 4B:
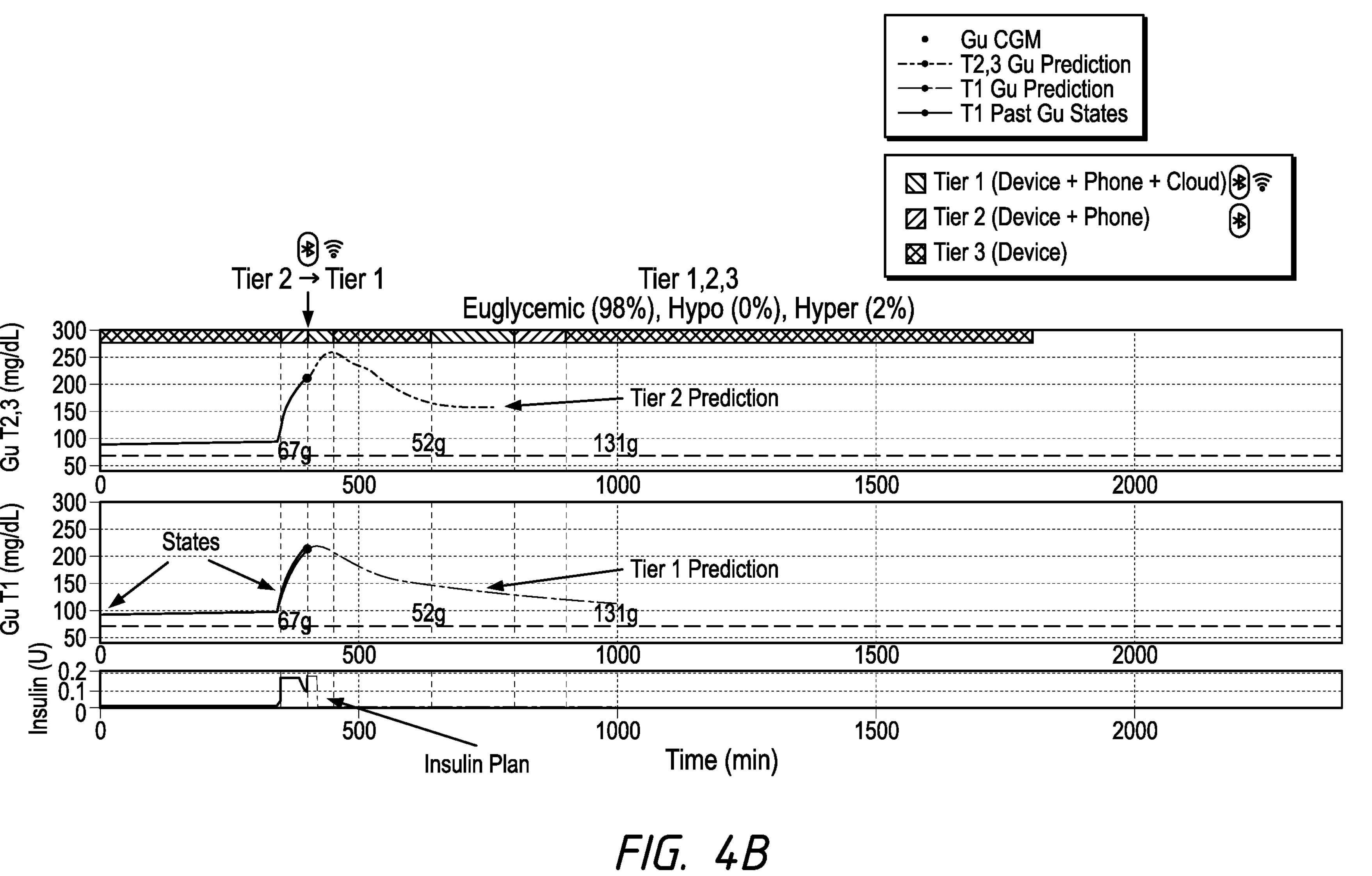
Figure 4C:
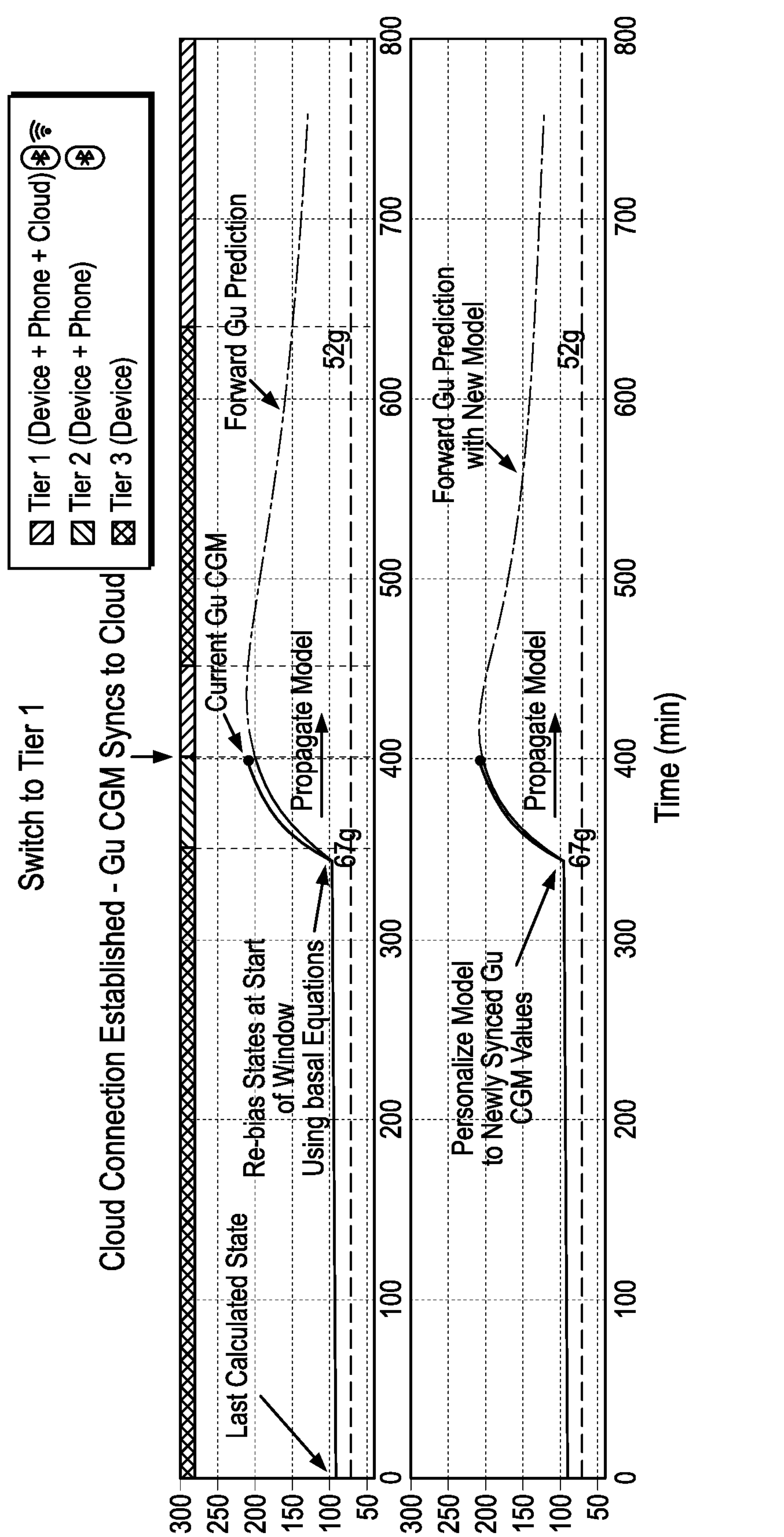
Figure 4D:
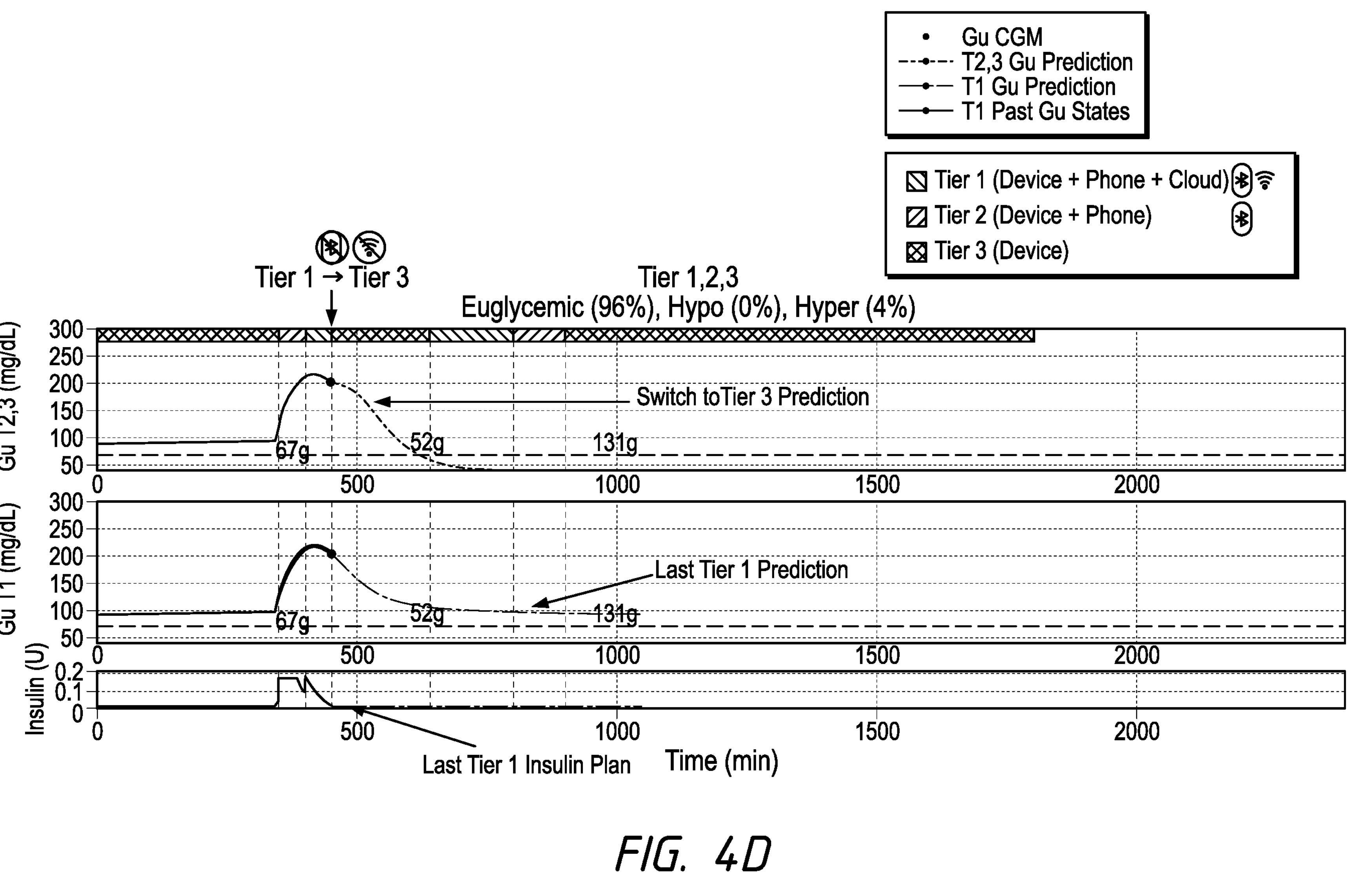

FIGS. 4A-4D illustrate example simulations of switching to different tiers using a tier switching algorithm, such as described with reference to FIGS. 3C and 3D. For example, FIG. 4A illustrates a simulation where a control system starts in Tier 3. When connection to the user device 304 is established, the system switches to Tier 2. The past logged meal of 67 g must then be incorporated into the glucose prediction. In another example, FIG. 4B illustrates an example simulation where cloud connection is established and the system switches from Tier 2 to Tier 1. Since the algorithms are different techniques, the prediction curve changes. Since the past states for the Tier 1 algorithm are unavailable due to the fact that this is the first time this algorithm is called, the past states must be calculated within the past window, indicated in magenta. The model is propagated forward until the current point in time and MPC is calculated to give the insulin plan. In another example, FIG. 4C illustrates an example graph showing more detail on the updates to the model. Initially, the model is biased to the glucose value at the start of the window and the model is propagated forward. Also, personalization is initiated to tune the model parameters to match the glucose CGM measurements. After personalization, the past model states and forward prediction both change. FIG. 4D illustrates an example simulation where both user device 304 connection and cloud connection are lost and the algorithm reverts back to Tier 3.

D. Example Glucose Prediction Engine

Figure 5A:
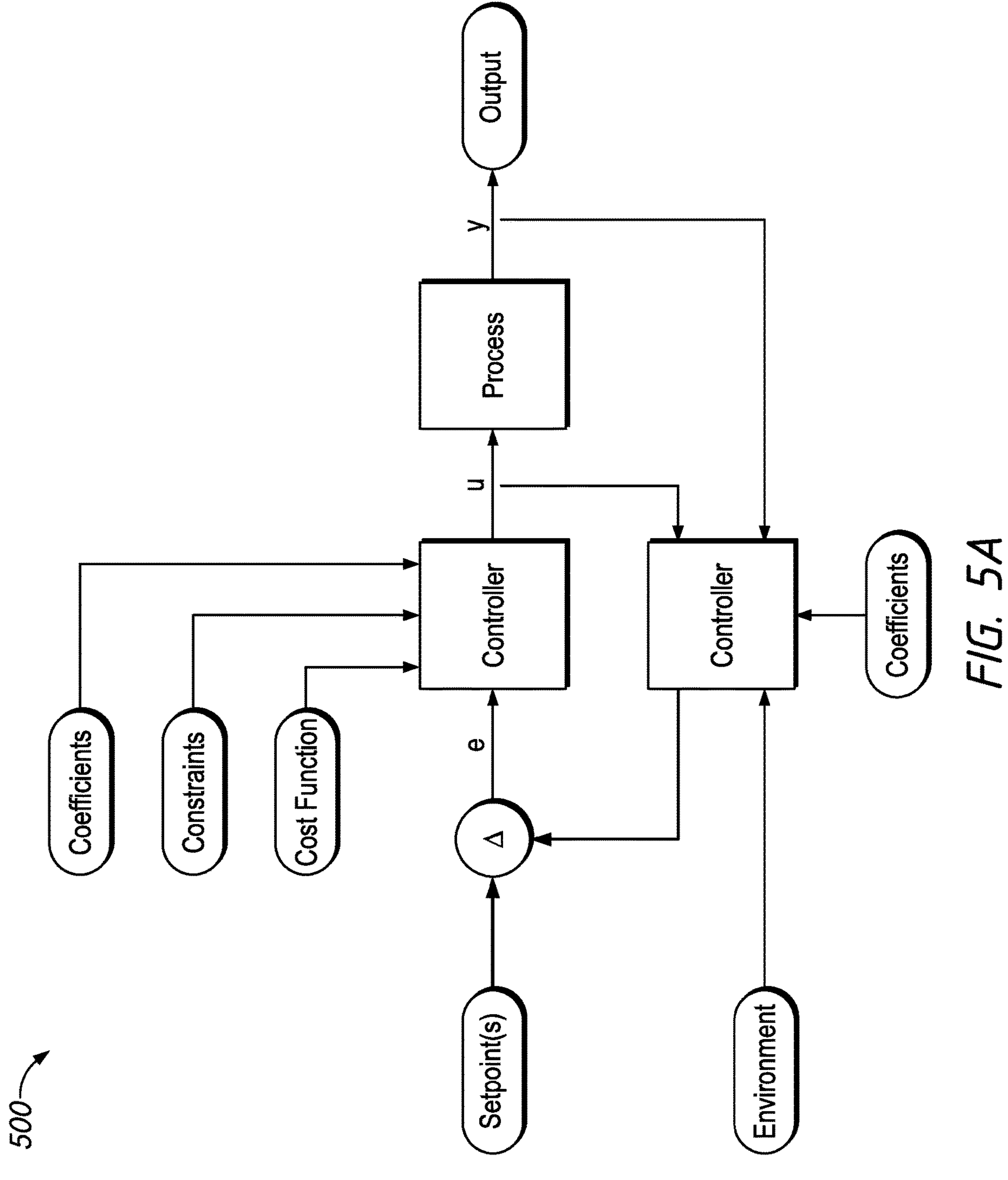
FIG. 5A illustrates an example MPC control system that may be part of a glucose prediction engine to generate control signals for one or more devices and/or notifications to a user in order to facilitate a desired outcome.

Model Predictive Control (MPC) is a process control technique that uses a predictive model for a complex system with constraints to provide control of a process. In some examples, a controller 1000 may utilize a MPC control process to utilize a physiological model of the user to predict future glucose values and determine the optimal sequence of stimuli (for example, an insulin bolus) necessary to achieve a desired outcome of, for example, a desired glucose response of a user. FIG. 5A illustrates an example MPC control system 500 that may be part of a glucose prediction engine 1004 used by a controller 1000 to generate control signals for one or more devices and/or notifications to a user in order to facilitate a desired outcome.

As illustrated in FIG. 5A, a controller may receive one or more inputs for a model, including but not limited to, one or more coefficients, one or more constraints, and a cost function. In some examples, the controller may receive an initial model with one or more initial setpoints or values. The controller may output a model, which can then be used as part of a control process. In some examples, the model may be updated based on one or more coefficients, environmental factors, outputs of a control process, the like or a combination thereof. The updated model may then be used by the controller.

In some examples, an MPC model can include a linear dynamical system. A linear MPC may use a linear system model in a prediction. However, other types of MPC systems may also be used, such as a nonlinear MPC. A state-space representation of a continuous-time linear MPC system can include:

$$\dot{x}(t)=A_{cts}x(t)+B_{cts}u(t)$$

$$y(t)=\text{Cctsx}(t)+\text{Dctsu}(t)$$

Where A is the state (or system) matrix, B is the input matrix, and x(t) is the state vector. In some examples, x(t) may represent states of the glucose control system, such as meal input information or insulin on board a device. In some examples, u(t) may represent a control signal, such as a quantity or presence of insulin or glucagon in a glucose control system. In some examples, y(t) can include observed values, such as a past history of glucose values. In some examples, Dcts may be a zero value.

Discretization of the state-space representation may be performed to obtain the discrete-time system:

$$X_{k+1}=A_d x_k+B_d u_k$$

$$y_k=C_d x_k$$

$$A_d=e^{t_s A_{cts}}$$

$$B_d=A_{cts}^{-1}(A_d-1)B_{cts}$$

$$C_d=C_{cts}$$

Error feedback $q_k$ may be added to the states to allow a solver to approach a reference target $r_k$. A cost function can be minimized on the difference between the desired glucose target and the actual glucose value so that the solver can find a set of inputs which will optimally converge to the target. However, there may not exist a solution which can reach the target within the given time horizon, so a slack variable $s_k$ is added to the error feedback to allow flexibility in not reaching the target. The scalar s provides a tuning parameter to control the allowed deviation from the target and the magnitude of the slack variable. Accordingly, the state-space representation may be written as:

$$\begin{bmatrix} \tilde{x}_{k+1} \\ q_{k+1} \\ r_{k+1} \end{bmatrix} = \begin{bmatrix} A_d & 0 & 0 \\ C_d & 0 & -I \\ 0 & 0 & I \end{bmatrix} \begin{bmatrix} \tilde{x}_k \\ q_k \\ r_k \end{bmatrix} + \begin{bmatrix} B_d & 0 \\ 0 & sI \\ 0 & 0 \end{bmatrix} \begin{bmatrix} \tilde{u}_k \\ s_k \end{bmatrix}$$

$$A = \begin{bmatrix} A_d & 0 & 0 \\ C_d & 0 & -I \\ 0 & 0 & I \end{bmatrix}$$

$$B = \begin{bmatrix} B_d & 0 \\ 0 & sI \\ 0 & 0 \end{bmatrix}$$

$$x_k = \begin{bmatrix} \tilde{x}_k \\ q_k \\ r_k \end{bmatrix}, u_k = \begin{bmatrix} \tilde{u}_k \\ s_k \end{bmatrix}$$

Iterative calls to the discrete state-space model for up to N time horizon steps will form the state propagation matrices.

$$x_1=Ax_0+Bu_0$$

$$x_2=Ax_1+Bu_1$$

Substituting yields:

$$x_2=A(Ax_0+Bu_0)+Bu_1$$

$$x_2=A^2x_0+ABu_0+Bu_1$$

Repeating this Procedure Yields:

$$\begin{bmatrix} x_1 \\ \vdots \\ x_N \end{bmatrix} = \begin{bmatrix} B & 0 & \cdots & 0 \\ AB & B & \cdots & 0 \\ \vdots & \vdots & \ddots & 0 \\ A^{N-1}B & A^{N-2}B & \cdots & B \end{bmatrix} \begin{bmatrix} u_0 \\ \vdots \\ u_{N-1} \end{bmatrix} + \begin{bmatrix} A \\ A^2 \\ \vdots \\ A^N \end{bmatrix} x_0$$

$$x = \begin{bmatrix} x_1 \\ \vdots \\ x_N \end{bmatrix}, \overline{S} = \begin{bmatrix} B & 0 & \cdots & 0 \\ AB & B & \cdots & 0 \\ \vdots & \vdots & \ddots & 0 \\ A^{N-1}B & A^{N-2}B & \cdots & B \end{bmatrix}, u = \begin{bmatrix} u_0 \\ \vdots \\ u_{N-1} \end{bmatrix}, \overline{T} = \begin{bmatrix} A \\ A^2 \\ \vdots \\ A^N \end{bmatrix}$$

Expanding the Cost Function:

$$J = \sum_{\tau=0}^{N} \left( x_\tau^T Q x_\tau + u_\tau^T R u_\tau \right)$$

$$J = x_0^T Q x_0 = [\,x_1^T \;\; \cdots \;\; x_N^T\,] \begin{bmatrix} Q & 0 & \cdots & 0 \\ 0 & Q & \cdots & 0 \\ 0 & \vdots & \ddots & 0 \\ 0 & 0 & \cdots & Q_f \end{bmatrix} \begin{bmatrix} x_1 \\ \vdots \\ x_N \end{bmatrix} + [\,u_0^T \;\; \cdots \;\; u_{N-1}^T\,] \begin{bmatrix} R & 0 & \cdots & 0 \\ 0 & R & \cdots & 0 \\ 0 & \vdots & \ddots & 0 \\ 0 & 0 & \cdots & R \end{bmatrix} \begin{bmatrix} u_0 \\ \vdots \\ u_{N-1} \end{bmatrix}$$

$$J = x_0^T Q x_0 + x^T \overline{Q} x + u^T \overline{R} u$$

Substituting Variables Yields:

$$x = \overline{S}u + \overline{T}x_0$$

$$J = x_0^T Q x_0 + x^T \overline{Q} x + u^T \overline{R} u$$

$$J = x_0^T Q x_0 + \left(\overline{S}u + \overline{T}x_0\right)^T \overline{Q} \left(\overline{S}u + \overline{T}x_0\right) + u^T \overline{R} u$$

$$J = \frac{1}{2} x_0^T 2\left(Q + \overline{T}^T \overline{QT}\right) x_0 + \frac{1}{2} u^T 2\left(\overline{R} + \overline{S}^T \overline{QS}\right) u + x_0^T 2 \overline{T}^T \overline{QS} u$$

$$J = \frac{1}{2} x_0^T \overline{Y} x_0 + \frac{1}{2} u^T \overline{H} u + \overline{F} u$$

The first term does not depend on u and hence is a constant to the cost function and can be removed. Accordingly, the cost function can be written as:

$$J = \frac{1}{2} u^T \overline{H} u + \overline{F} u$$

Wherein the inputs u can be solved for with a quadratic programming solver. An optimization of the cost function J using the control inputs u may be used to direct activity of the medical control system, such as one or more glucose control devices. In this way, an MPC system may anticipate future events by solving a predictive model, such as a glucose prediction model (for example, GIMM), and take control actions accordingly.

E. Example Model Processing

Depending on the size of the model that the MPC uses, it can be a difficult task to move MPC processes to an embedded system. For example, due to memory constraints and solving of the quadratic problem at every time step, an embedded system may not be configured to handle the required computational load. Systems and methods of reducing memory and computational requirements for an MPC based control system are described herein. In some examples, if computational requirements cannot be adequately addressed, then MPC processes may be split over a plurality of devices.

Memory requirements may scale with the polynomial space complexity of $O(n^2)$ or $O(n^3)$ from the size, n, of the state and input matrices. Thus, extra care should be taken to reduce the size to the essential components in order to reduce the memory requirements. Many matrices are banded (elements fall near diagonal) or sparse (contain many zeros), which means the storage can be significantly reduced by only storing the nonzero elements. However, this trade-off may have a negative impact on computation time of non-sparse matrices, overhead in storage of element locations, and may limit code reusability and simplicity. Therefore, extra effort must be dedicated to tailoring custom matrix manipulation functions for both sparse and non-sparse matrices.

A convex quadratic program (QP) can be solved in polynomial time with the interior-point method. However, in the case of a non-convex QP, the active-set method may be used, which is NP-hard and may not converge to a solution. Therefore, the system must verify that the matrix is properly conditioned to ensure a bounded computation time and convergence to a solution. Exploiting sparsity may also aid in computation time at the expense of code size.

Discretization of a continuous time state space system may be useful to model the dynamics of a Glucose Predictor model, such as a Glucose Insulin Meal Model (GIMM), on a processor. However, calculating a matrix exponential at every iteration is a very computationally intensive operation and may not be feasible in real-time. Therefore, the forward Euler Method or Runge-Kutta method (RK4) may be utilized to approximate the derivative of the differential equation. Advantageously, this can enable a relatively good approximation with a reasonable computation time.

Model Predictive Control can be formulated as a quadratic program (QP). Depending on the exact formulation of the problem, some solvers may be optimized for specific use cases with limited functionality. For example, inequality constraints on the state or input variables can be soft or hard, self-correlated or cross-correlated, or require an affine transformation. Most solvers rely on numerical methods which converge toward a solution in a fixed maximum number of iterations to ensure the program will finish in a finite amount of time. Certain methods for solving a system of linear equations can be robust, such as avoiding divisions by zeros, to guarantee stability and efficiency. However, because of numerical approximations and rounding error, a solution will not be an exact solution. This error can be propagated forward over time and cause the system to drift in an undesirable direction. Disclosed herein include methods to stabilize an MPC model. In some examples, the system may undergo periodic realignment, as known observations, such as CGM glucose values, accumulate and are acquired by the system. In another example, noise estimation in the form of a Kalman filter can be introduced to allow the system to be robust in the case of noise sources.

F. Glucose Insulin Meal Model and MPC

An MPC control process may be configured to utilize a physiological model of the user to predict future glucose values and determine the optimal sequence of stimuli (for example, an insulin bolus) necessary to achieve a desired outcome of, for example, a desired glucose response of a user. In some examples, a physiological model used with MPC can include a Glucose Insulin Meal Model.

However, a Glucose Insulin Meal Model (GIMM) may be nonlinear in its dynamics and require a nonlinear MPC solver. Although nonlinear MPC solvers have seen huge advancements in recent decades, the problems of convergence, stability, and computation time still remain. Linear MPCs can be solved with a variety of Quadratic Programming (QP) solvers and a solution can be reached in polynomial time if the problem can be proven to be convex. A QP solver can be shown mathematically to be convex if the Hessian is positive semidefinite. Also, all calculus rules and transformations prior to the QP can be traced to validate if they preserve convexity. Given that a solver may be running on an embedded processor in certain implementations, it may be desirable to limit the problem to be linear and convex will in order to allow the solution to be realizable.

The nonlinear functions in GIMM can be linearized at a specific operating point using a first order Taylor series expansion:

$$f(x, y) \approx f(x_0, y_0) + \frac{\partial f}{\partial x}|_{x_0,y_0}(x - x_0) + \frac{\partial f}{\partial y}|_{x_0,y_0}(y - y_0)$$

Linearization may only be valid very close to the operating point. Since the linearization depends on the current value of the state variable, it needs to be reevaluated multiple times at iterations of the control loop. Also, since the linearization changes as the system evolves, the new linearization should be reflected in the propagation of the state and input matrices. For example, in the traditional QP formulation, state and input matrix propagation has the form:

$$\begin{bmatrix} B & 0 & \dots & 0 \\ AB & B & \dots & 0 \\ \vdots & \vdots & \ddots & 0 \\ A^{N-1}B & A^{N-2}B & \dots & B \end{bmatrix}$$

However, with the linearization of the state matrix, the matrix propagation has the form:

$$\begin{bmatrix} B & 0 & \cdots & 0 \\ A_1 B & B & \cdots & 0 \\ \vdots & \vdots & \ddots & 0 \\ A_{N-1} \cdots A_2 A_1 B & A_{N-2} \cdots A_2 A_1 B & \cdots & B \end{bmatrix}$$

Since the future state matrices $A_1, A_2, \ldots A_{N-1}$ depend on the unknown future states, linearizing these matrices can be difficult. However, the inputs, such as insulin, may be restricted to be nonnegative, so the direction can be predicted given the current state. Also, initial guesses or values may be used for future state matrices, including but not limited to the warm start state and input matrices from a previous iteration.

One or more parameters of a predictive model may be linearized. For example, an insulin-dependent glucose utilization ($U_{id}$) may be linearized as follows:

$$U_{id}(X, G_c) = \frac{(V_{m0} + V_{mx}X)G_t}{K_{m0} + G_t}$$

$$\frac{\partial U_{id}}{\partial X} = \frac{V_{mx}G_t}{K_{m0} + G_t}$$

$$\frac{\partial U_{id}}{\partial G_c} = \frac{(V_{m0} + V_{mx}X)K_{m0}}{(K_{m0} + G_{L0})^2}$$

$$U_{id}(X, G_t) \approx \frac{(V_{m0} + V_{mx}X_0)G_{t0}}{K_{m0} + G_{t0}} + \frac{V_{mx}G_{t0}}{K_{m0} + G_{t0}}(X - X_0) + \frac{(V_{m0} + V_{mx}X_0)K_{m0}}{(K_{m0} + G_{t0})^2}(G_t - G_{t0})$$

The rate of stomach emptying into the gut ($k_{empt}$) may be linearized as follows:

$$k_{empt}(Q_{stol}, Q_{sto2}) = Q_{sto2}\left[k_{max} + \frac{k_{max} - k_{min}}{2}\{\tanh[\alpha(Q_{sto1} + Q_{sto2} - bD)] - \tanh[\beta(Q_{sto1} + Q_{sto2} - cD)]\}\right]$$

$$f_0 = \left[k_{max} + \frac{k_{max} - k_{min}}{2}\{\tanh[\alpha(Q_{sto1,0} + Q_{sto2,0} - bD)] - \tanh[\beta(Q_{sto1,0} + Q_{sto2,0} - cD)]\}\right]$$

$$df_0 = Q_{sto2,\beta}\left[\frac{k_{max} - k_{min}}{2}\{\alpha[1 - \tanh^2[\alpha(Q_{sto1,0} + Q_{sto2,0} - bD)]] - \beta[1 - \tanh^2[\beta(Q_{sto1,0} + Q_{sto2,0} - cD)]]\}\right] k_{empt}(Q_{sto1}, Q_{sto2}) \approx Q_{sto2,0} * f_0 + (Q_{sto1} - df_0) + (Q_{sto2} - f_0 - df_0)$$

The rate of insulin depletion based on hepatic efficiency may be linearized as follows:

$$m_3(I_L, I_{po}) = m_1 \frac{m_6 - m_5\gamma I_{po}}{1 + m_5\gamma I_{po} - m_6} I_L$$

$$\frac{\partial m_3}{\partial I_L} = m_1 \frac{m_6 - m_5\gamma I_{po}}{1 + m_5\gamma I_{po} - m_6}$$

$$\frac{\partial m_3}{\partial I_{po}} = \frac{-m_1 m_5 \gamma I_L}{(1 + m_5\gamma I_{po} - m_6)^2}$$

$$m_3(I_L, I_{po}) \approx m_1\left[\frac{m_6 - m_5\gamma I_{po,0}}{1 + m_5\gamma I_{po,0} - m_6} I_{L,0} + \frac{m_6 - m_5\gamma I_{po,0}}{1 + m_5\gamma I_{po,0} - m_6}(I_L - I_{L,0}) + \frac{-m_1 m_5 \gamma I_{L,0}}{(1 + m_5\gamma I_{po} - m_6)^2}(I_{po} - I_{po,0})\right]$$

Other linearizations of other parameters may also be possible. As noted above, use of one or more linearizations may allow for a more realizable solution for a predictive model. This may allow for faster results, better control of a medical control device or medical control system, and/or the ability to run a MPC model on an embedded system.

G. Example Methods of Improving MPC Stability

Although MPC can greatly improve time in range of a patient, it may present faults and can be prone to instability from many competing factors, such as wrongly chosen personalization coefficients, incorrectly chosen time horizons, an infeasible control problem, wrongly user entered stimuli (input saturation), linearization error, and overly aggressive tuning that could result in unexpected behavior. Although this may be the case, MPC remains adaptive at every time step and continually recalibrates. Another way to help address this is by using a smaller linear program which can be solved to determine if there exists a feasible solution given the current state and the state and input constraints. By solving this problem, one may also determine the number of iterations for which the system remains in the feasible set. Systems and methods described herein may help identify and mitigate concerns surrounding instability of a MPC system.

Factors related to determining if there exists a feasible solution can include, but is not limited to: current maximum allowable values for every state in non-linear confidence interval from glucose insulin meal model (GIMM), current & horizon maximum allowable values for every state in linear MPC model, controllability rank in linear MPC model, observability rank in linear MPC model, whether eigenvalues of A have a negative real part in linear MPC model, agreement of states shared between linear MPC model and non-linear GIMM, agreement of non-linear GIMM CGM glucose prediction and actual observed CGM glucose, and ensembles agreement of unique controller output algorithms (MPC complex, MPC simple, PID, Fuzzy).

For example, since the integral of a constant differential equation results in an exponential equation, any positive constants would cause the equation to approach infinity as time goes to infinity, thus resulting in instability of the system. Therefore, stability is guaranteed if the eigenvalues have a negative real part since the system will decay to zero as time goes to infinity. Since the state matrix is linearized at different iterations, the matrix should be periodically reevaluated for stability to ensure convergence in the solution.

Other forms of error reduction may also be used. For example, a controller may use slack variables to ensure non-negative error with respect to target.

Another way to address system instability can be by using eigenvalues. Since the integral of a constant differential equation results in an exponential equation, any positive constants would cause the equation to approach infinity as time goes to infinity, thus resulting in instability of the system. Therefore, stability is guaranteed if the eigenvalues have a negative real part since the system will decay to zero as time goes to infinity. Since the state matrix is linearized at each iteration, the matrix needs to be reevaluated for stability to ensure convergence in the solution.

A solution may be aggressive and personalized to an individual or loosely adapted to an individual and generic to ensure insulin is dosed in a safe way. In the first solution mentioned above, in order to achieve a high time in range (TIR), the controller needs to be aggressive in adapting to both short and long-term changes in user behavior. A caveat to being overly aggressive is higher change of instability since many unknown parameters are being estimated. Therefore, the system will keep track of specific parameters (states or eigenvalues) to work well for a user over a long period of time. This personalized controller will be used in the event of detecting instability in the aggressive controller. Since the personalized controller may require adaptation to user-specific parameters, it may also have instability if user's behavior is erratic or unpredictable. In such a situation, a generic controller would be implemented representing the average person. This controller would be validated over a large population and shown to be safe in all circumstances.

Personalization can have an improvement on closed loop stability and performance as well. This necessitates the input learning of many external values such as food type, quantity, timing, insulin sensitivity, sleep, weight, gender, age, metadata, preferred insertion site, the like or a combination thereof. Given that users can vary widely among the population in their total insulin usage and sensitivity to insulin, variables such as peripheral insulin sensitivity and hepatic insulin sensitivity may be updated or personalized to provide accurate estimation to keep the user in tight euglycemic control. These variables may be initialized primarily using body weight, but can use other secondary metadata, such as age, gender, and preferred insertion site, if supplied by the user, which can further classify the user into a narrower distribution. In some examples, advanced users may be allowed to directly modify their insulin sensitivity. Advantageously, this may allow advanced users to exert control that they may be accustomed to with other products that allows the users to modify their insulin sensitivity.

Insulin sensitivity may change over time. Accordingly, insulin sensitivity may be adapted over time as a user's specific needs will fluctuate with diet, exercise, general health, advancement of disease state, stress, caffeine, menstrual cycles, the like or a combination thereof. Therefore, analysis of historical data may be used in recognizing patterns in user behavior and response to insulin. An example of a pattern that may be determined based on an analysis of historical data can include having a predicted insulin sensitivity factor lower than the actual value. For example, a closed loop system may inadvertently dose a large amount of insulin, causing the user's glucose level to drop below the low threshold. As a safety mechanism, the insulin delivery system may turn off and notify the user to eat carbohydrates to bring his/her glucose level back to baseline. As the glucose levels begin to rise above the low threshold, the insulin delivery system may switch on and again attempt to dose a large amount of insulin. In order to break this unfavorable cycle, the closed loop system may notice or determine a pattern that the user is more responsive to insulin than previously estimated, and therefore lower the insulin dosage appropriately.

H. Personalization of MPC Models

A controller of a control system may utilize one or more methods to mitigate a detected or anticipated instability of the MPC system. For example, a controller may perform one or more processes for reducing user error, such as introduced with user input, from the closed loop system. In some examples, a closed loop system may utilize one or more parameters that are personalized for a user and are anticipated to result in a more stable controller. The personalized controller may be useful to achieve higher time in range (TIR) because, in order to achieve a high TIR, the controller may be configured to be aggressive in adapting to both short and long-term changes in user behavior. However, an overly aggressive controller has an increased chance of instability due to estimation of many unknown parameters in the system. In order to reduce the risk of instability, a closed loop system may keep track of one or more parameters that are estimated or known to work well for a user. For example, the one or more parameters may be identified as working well and/or resulting in a more stable controller for a user over a threshold period or length of time, such as a number of hours or days. This personalized controller will be used in the event of detecting instability in the aggressive controller.

However, since a personalized controller may require adaptation to user-specific parameters, it may also have instability if a user's behavior is erratic or unpredictable. For example, if a user fails to input accurate insulin or meal information, instability may occur. In such a situation, a generic controller can be implemented that is configured to represent the average person. This generalized controller can be validated using, for example, data from a population of users or clinical testing and shown to be safe in for use across a broad range of users. In some examples, a generalized controller may be adapted for one or more demographics of a user, such as a height, weight, diagnosis, A1C value, other physiological parameter, the like or a combination thereof.

In some examples, a personalized controller may be configured to change a controller state to a previously stable personalized controller, a safe mode for an MPC controller, or another controller state that may have reduced instability from the previous controller state. In some examples, a control system may move a user out of a closed loop mode. A control system may include one or more arbitrators or controller ensembles in order to facilitate a change between controller states.

Figure 5B:
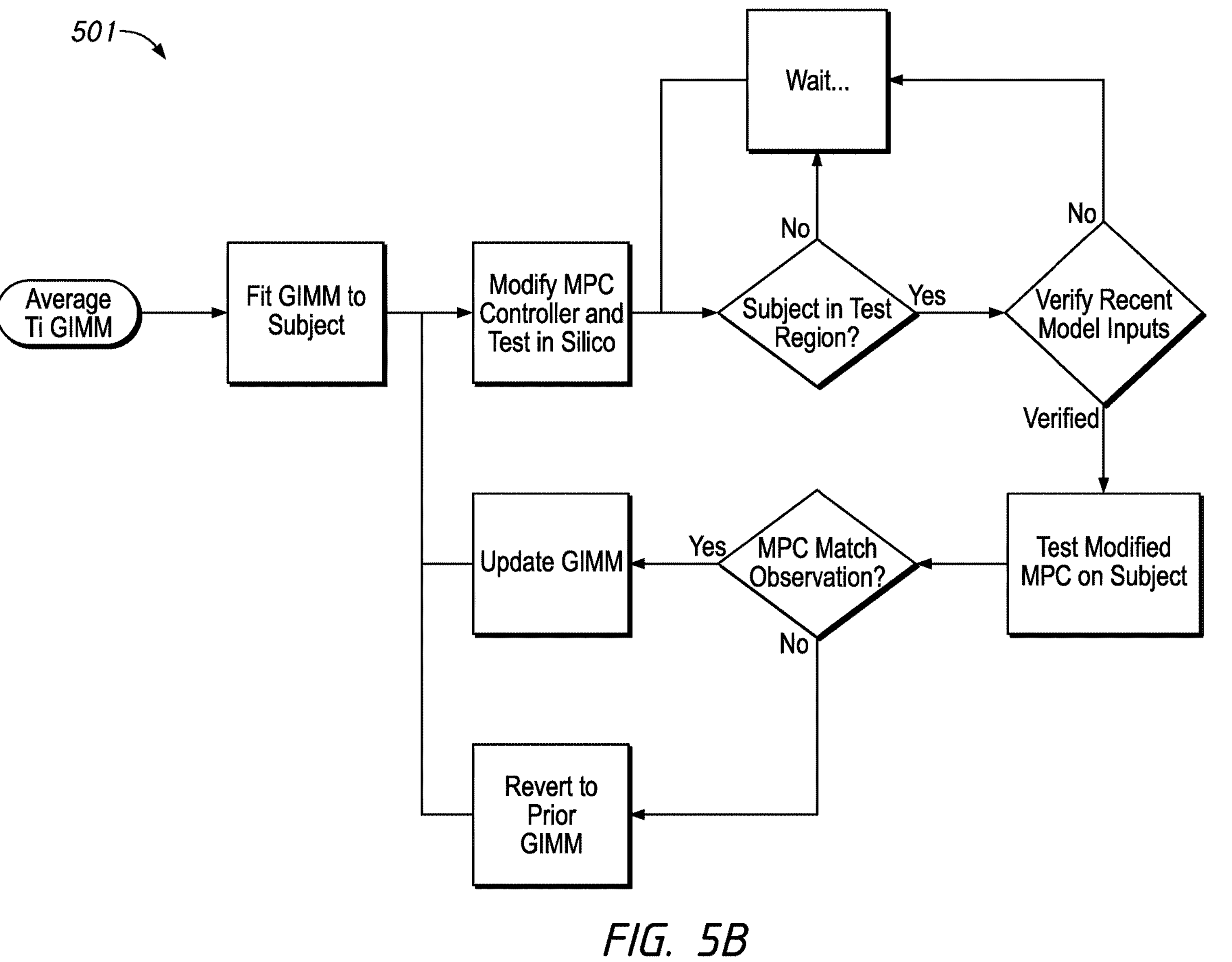
FIG. 5B illustrates an example self-learning or personalization process for a model or model parameters that may help tighten glucose control in a glucose control system.

FIG. 5B illustrates an example self-learning or personalization process 501 for a model or model parameters that may help tighten glucose control in a glucose control system. For example, as illustrated in FIG. 5B, an average model, such as an average or standardized model for a demographic associated with the user, such as Type 1 diabetes, may be personalized by a controller. The controller may fit the prediction from the model to the subject using a data collected in relation to the subject. The controller may then modify the MPC control system parameters and perform an artificial (or computational) test to determine if the resulting prediction is within a target region. If the result is satisfactory, the controller may verify the recent model inputs and test the modified MPC on the user themselves. If the result is not satisfactory, then the system may further modify the MPC control system parameters until an end condition is met, such as a satisfactory result or another exit condition. As noted above, if the result is satisfactory and the controller tests the modified MPC on the user, the controller may determine if the model prediction matches an observation. If the prediction matches the observation, the controller may modify the input parameters to the model to personalize it to the user. If the prediction does not match the observation, then the controller may revert the input parameters to the prior input parameters.

a. A Predictive Model that Prevents Hypoglycemia

In order for the control algorithm to foresee the consequences of an insulin dosage, an algorithm should have a prediction horizon that extends towards the full action of insulin. This can be an extended time period. For example, in the case of fast-acting insulin, the duration of insulin activity can be as long as 6 hours. However, propagation of the state and input matrices for a glucose insulin meal model over such a long duration can be expensive in both computational and memory requirements. Therefore, an accelerated version of the propagation matrices may be used to quickly reach the prediction horizon with reasonably sized constraints. Additionally or alternatively, a hybrid approach with a mixture of short-term and long-term propagation can be formulated, which strikes a balance between realizability and effectiveness. However, since the fixed time step assumption may be violated, further investigation may be used to validate the feasibility of the problem.

Since a controller of the closed loop system will plan out insulin dosages from the present until the end of the duration of insulin activity, the algorithm will be able to detect and avoid hypoglycemic events. A heavy cost can be incurred in the cost function corresponding to varying levels of severity and the controller may plan accordingly to avoid those circumstances. Since the plan is recalculated at every iteration, the controller may be able to adjust its plan accordingly either if the initial plan was too aggressive or if the circumstances have changed. In this way, MPC may be adaptive to differences in the model and actual measured data to avoid hypoglycemia in both scenarios.

b. Detection of Insulin or Meal Bolus

Different stimuli, such as the input of food or exercise may be difficult to measure and account for in a medical device control system. In one example, food stimuli (or a food bolus) may be difficult to measure in persons with type 1 diabetes. The difficulty can arise from the fact that to accurately predict glucose appearance in blood one must accurately quantify, classify, and make time estimates of ingestion. Some systems may rely on user input to address this issue. However, user input accuracy can be poor and reliance on such may result in inaccurate insulin control in a medical device control system. Described herein are processes for validation of and retrospective prediction of quantities associated with food or other bolus with and without user description of those stimuli.

Since it is difficult for a model to fully predict the complex dynamics of the human body, corrections may be implemented to compensate for deviations of the model from actual data. These deviations can cover some combination of factors that are not incorporated in the model and factors that exist in the model but may not be reported by the user. Additionally or alternatively, inputs reported by the user may incorporate human error in estimation of meal sizes and nutritional content. Therefore, the model needs to be robust when accounting for these errors.

As more data is collected from the user, the glucose values can be used to retrospectively validate predictions on past meal and unknown states. As the prediction algorithm evolves and the prediction confidence grows, the user may be notified of predictions and can be asked to verify if, in fact, an unannounced meal or insulin did take place.

In some examples, a control system may be configured to update one or more parameters of a controller in response to detection of a deviation of at least one input from an estimated value. For example, a control system may be configured to update insulin or meal bolus information based on one or more expected insulin or meal values not matching with input insulin or meal values.

Figure 5C:
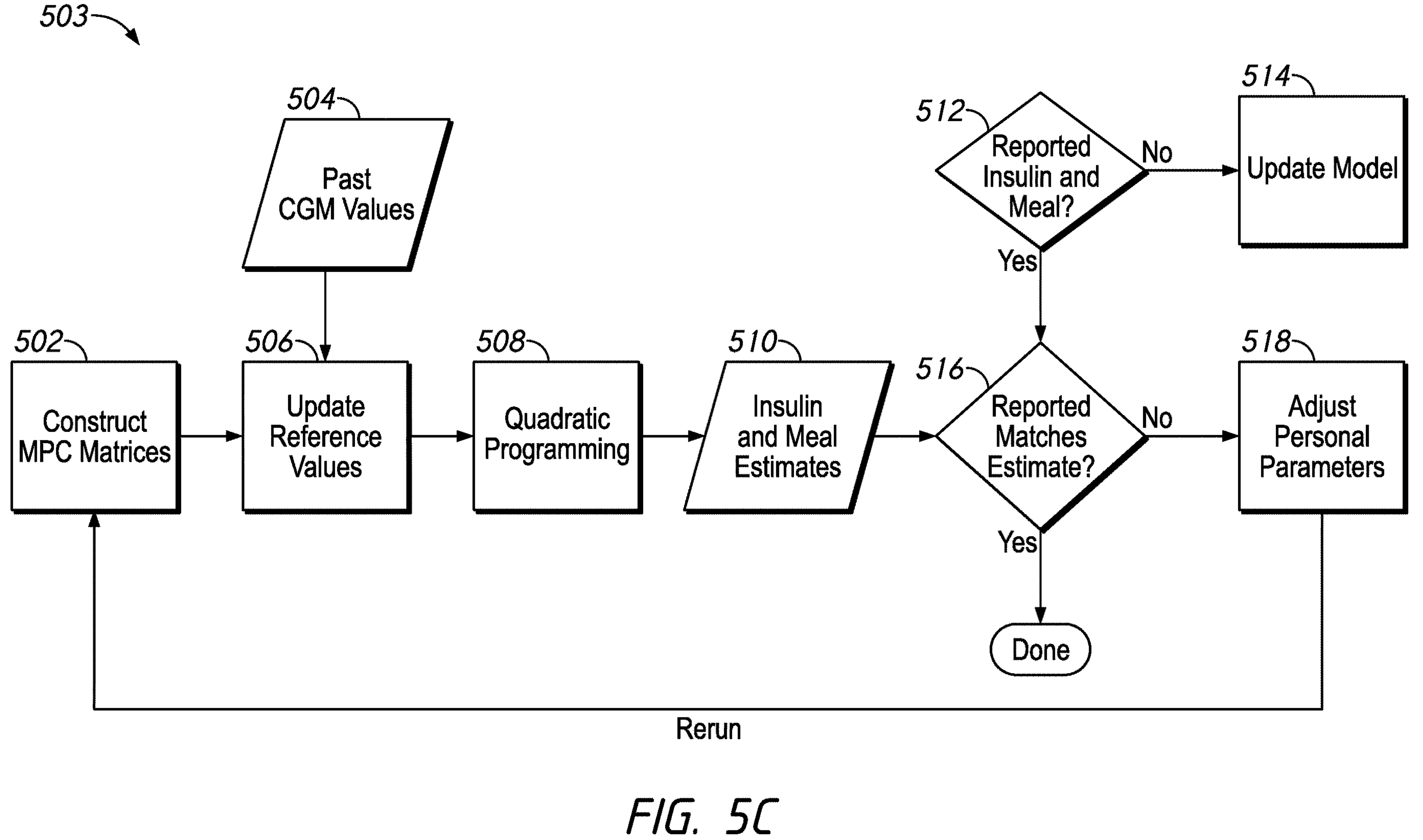
FIG. 5C illustrates an example adjustment process that may be configured to update one or more controller parameters based on one or more model estimates.

FIG. 5C illustrates an example adjustment process 500 that may be configured to update one or more controller parameters based on one or more model estimates. For example, an adjustment process 500 can include, but is not limited to, an MPC construction block 502, a reference update block 506, a quadratic programming block 507, a reporting check block 512, a model update block 514, a matching check block 516, and a parameter adjustment block 518.

An MPC controller may solve for future insulin inputs to reach a reference target in a given time horizon. At a block 502, a control system may construct an MPC matrix. The MPC matrix may be constructed, for example, based on one or more input values, such as meal or insulin information. Using a similar MPC formulation as described above, the problem can be augmented to detect and quantify unreported insulin or meal boluses. At a block 506, a control system may update reference values. For example, the input matrix B can be updated to include both meal and insulin. At a block 508, the quadratic program can solve for the optimal past insulin and meal inputs 510 which exhibits the observed glucose profile by comparing the model glucose with the past glucose values as the reference values $r_k$. At a block 516, the timing and quantity of these insulin and meal inputs can be compared with the reported values, if any, and the discrepancy may help personalize the model for the subject at a block 518. The control may determine at a block 512 if values are not reported and/or whether the solved insulin and meal inputs are substantial. If the values are not reported, then the system has detected an unplanned event and can take appropriate action at a block 514 to adjust parameters of the system.

The only matrix that depends on the initial state $x_0$ is the matrix $\overline{T}$, so only $\overline{T}$ needs to be modified to switch from a single reference target $r_0$ to a vector of past glucose values $r_0, r_1, \ldots, r_{N-1}$:

$$\overline{T}x_0 = \begin{bmatrix} A \\ A^2 \\ \vdots \\ A^N \end{bmatrix} \begin{bmatrix} \tilde{x}_0 \\ q_0 \\ r_0 \end{bmatrix} = \begin{bmatrix} A_d & 0 & 0 \\ C_d & 0 & -I \\ 0 & 0 & I \\ A_d^2 & 0 & 0 \\ C_d^2 & 0 & -I \\ 0 & 0 & I \\ \vdots & \vdots & \vdots \\ A_d^n & 0 & 0 \\ C_n^d & 0 & 0 \\ 0 & 0 & I \end{bmatrix} \begin{bmatrix} \tilde{x}_0 \\ q_0 \\ r_0 \end{bmatrix} = \begin{bmatrix} A_d\tilde{x}_0 \\ C_d\tilde{x}_0 - r_0 \\ r_0 \\ A_d^2\tilde{x}_0 \\ C_d^2\tilde{x}_0 - r_0 \\ r_0 \\ \vdots \\ A_d^n\tilde{x}_0 \\ C_d^n\tilde{x}_0 - r_0 \\ r_0 \end{bmatrix}$$

Accordingly, $\overline{T}$ Becomes:

$$\overline{T}x_0 = \begin{bmatrix} A_d\tilde{x}_0 \\ C_d\tilde{x}_0 - r_0 \\ r_0 \\ A_d^2\tilde{x}_0 \\ C_d^2\tilde{x}_0 - r_0 \\ r_0 \\ \vdots \\ A_d^n\tilde{x}_0 \\ C_d^n\tilde{x}_0 - r_0 \\ r_0 \end{bmatrix}$$

The most important personalization parameters to solve for are the carbohydrate and insulin sensitivity. Using the meal and insulin estimates and comparing them to the user reported meal and insulin amounts, the ratio can be determined, and a correction factor can be applied to the model parameters. The model is then rerun with the updated patient parameters and then the new meal and insulin estimates reevaluated to determine if they are closer to the reported values. Using this iterative approach, the patient parameters can be tuned to each subject.

Since the parameter estimation problem is a nonlinear problem, it can be approached from two angles. A heuristic method can be used to initialize the model from many different starting points, and each simulation can be compared with the true values to determine which is the closest. A nonlinear solver approach, such as the Levenberg-Marquardt, Gauss-Newton algorithm, or gradient descent, can be used to iteratively approach the solution by minimizing a cost function. The drawback is that the solver may remain in a local minimum, so a combination of both techniques may be used.

Figure 6:
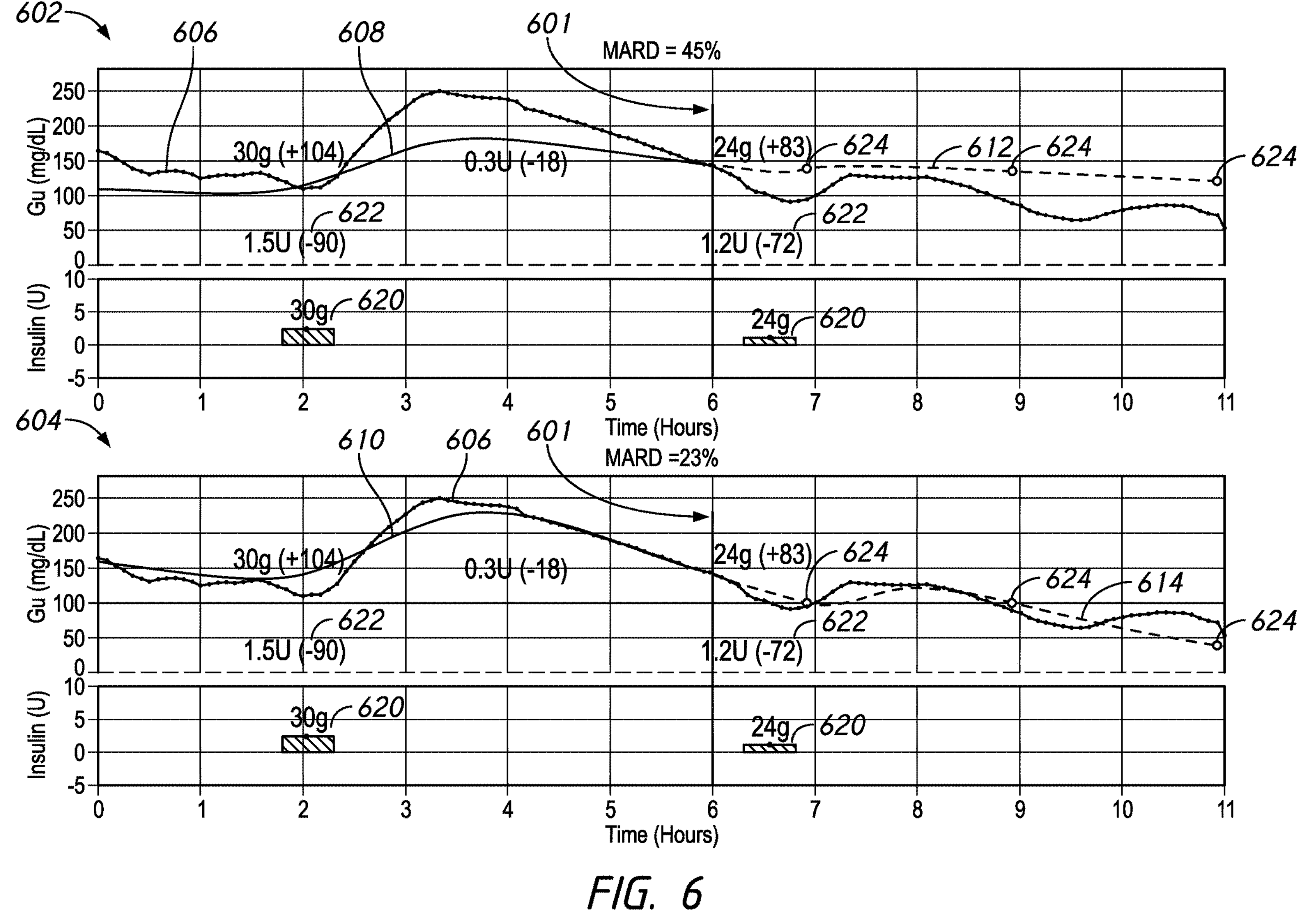
FIG. 6 illustrates examples of blood glucose estimation based on real CGM data with and without personalization.

FIG. 6 illustrates examples of blood glucose estimation based on real CGM data without personalization in graph 602 and with personalization in graph 604. As illustrated, line 606 represents CGM data in both graphs 602 and 604. Lines 608 and 610 illustrate data in graphs 602 and 604 that may be used to train a model, such as a GIMM model. Lines 612 and 614 illustrate predictions into a future time without and with personalization respectively. In some examples, a future time may include a time 601, which may correspond to one or more points in time after the end of data 608 or 610 used to train a model. In the illustrated example, a meal intake 620 in grams of carbohydrates are indicated at a 2-hour mark and approximately a 6.5 hour mark. In the illustrated an insulin bolus 622 in Insulin Units (U) and approximate expected decrease in glucose are indicated at approximately a 2-hour mark and approximately a 6.5 hour mark. Dots 624 indicate points of interest where the value of the Mean Absolute Relative Difference (MARD) is evaluated.

A prediction 614 may be more accurate with relation to actual CGM data 606 when a model is personalized. For example, as illustrated in graph 602, data 508 used to train a model may not be as true to actual glucose data 606 as data 610 illustrated in graph 604. Additionally, predictions 612 in a non-personalized model may not be as true to actual glucose data 606 as predictions 614 in a personalized model.

In some examples, one or more personalization parameters may include user supplied information, including but not limited to, age, height, insulin sensitivity, and carbohydrate ratio, the like or a combination thereof. In some examples, the user supplied information may be verified or validated by one or more processes or engines of the control system. For example, a control system may use one or more of a variable initialization function, such as a lookup table or experimentally determined function or other initial value or set of values.

In some examples, a control system may perform online and/or offline optimizations or refinements of a model, such as a non-linear GIMM or linear MPC model. Optimizations or refinements may include but are not limited to optimizations or refinements using multi-parameter modifier variables, such as peripheral insulin sensitivity or hepatic insulin sensitivity. Online and offline optimizations or refinements of a non-linear GIMM and/or linear MPC model may be performed with critical specific model parameters such as k1 or m3. Given that users vary widely among the population in their total insulin usage and sensitivity to insulin, variables such as peripheral insulin sensitivity and hepatic insulin sensitivity may require accurate estimation to keep the user in tight euglycemic control. These variables can be initialized using parameters, such as body weight, or other secondary metadata, such as age, gender, and preferred insertion site, if supplied by the user, which can further classify the user into a narrower distribution. Advanced users may be allowed to directly modify their insulin sensitivity, as they may already be accustomed to do so with other similar products.

Insulin sensitivity may also require adaptation over time as a user's specific needs fluctuate with diet, exercise, general health, advancement of disease state, stress, caffeine, menstrual cycles, or other lifestyle or health factors. Therefore, a control system may be configured to analyze or make use of an analysis of historical data in recognizing patterns in user behavior and response to insulin. The recognized patterns may then be used to personalize the model.

An example of a pattern involves having a predicted insulin sensitivity factor lower than the actual value. The system will inadvertently dose a large amount of insulin, causing the user's glucose level to drop below the low threshold. As a safety mechanism, the insulin delivery system may turn off and notify the user to eat carbohydrates to bring his/her glucose level back to baseline. As the glucose levels begin to rise above the low threshold, the insulin delivery system will switch on and again attempt to dose a large amount of insulin. In order to break this cycle, the system may be configured to notice that the user is more responsive to insulin than previously estimated and lower the insulin dosage appropriately.

I. Alternative Model for Closed Loop Control

In some examples, a performance of a control system may be improved using an Autoregressive Model with Exogenous Input (ARX). Performance of MPC can highly rely on how accurately the MPC model represents the actual system dynamics. As an alternative to using non-linear GIMM or locally linearized GIMM, empirical models identified from historical user data can also be used to predict future glucose trends.

An empirical dynamic autoregressive exogenous input (ARX) models identified from user data can be used to characterize the underlying relationship between system inputs (meal and insulin) and output (user glucose level).

$$y_{k+1} = \sum_{i=1}^{n_a} a_i y_{k-i+1} + \sum_{i=1}^{n_b} b_i u_{k-i+1}$$

The estimation of ARX model parameters may be achieved by Least Square estimation that minimizes the sum of square of one-step prediction errors. The Least Square solution for model parameter estimation is computationally efficient with a global minimum guaranteed. Once the ARX model parameters are estimated using user data, the model may be integrated into MPC to generate the prediction of a glucose trend for the prediction horizon.

In a 1-step prediction:

$$\hat{y}_{k+1} = \sum_{i=1}^{n_a} a_i y_{k-i+1} + \sum_{i=1}^{n_b} b_i u_{k-i+1}$$

The k-steps prediction into the future is generated from current time by performing the 1-step prediction iteratively, $$\hat{y}_{k+f} = \sum_{i=1}^{n_a} a_i \hat{y}_{k+f-i+1} + \sum_{i=1}^{n_b} b_i u_{k+f-i+1}$$

Since the ARX model parameters are estimated based on the user-specific data, the model is personalized for the user.

An ARX model may be updated over time to accommodate changes in glucose-insulin dynamics over time. To ensure the ideal performance of MPC under changing conditions, the ARX model may be identified and updated in a recursive fashion such that the model is adaptive to the new conditions. This adaptation mechanism can re-identify and update the model parameters as new CGM data and user input data, such as registered meal and insulin data, become available, and thus ensures that the most accurate model parameters estimated from the most recent data are used by MPC in glucose predictions.

J. Lipid Measurements in Closed Loop Control

The use of lipid information gives a substantial improvement over existing closed loop control systems, both reactive and hybrid. Current hybrid models of closed loop control rely on a user to give accurate estimations of the food they consume in order to appropriately dose insulin. Lipid measurements can play a role in dosing algorithms in hybrid closed loop control.

There are three main factors to consider while making a hybrid closed loop meal entry: (1) start time of food ingestion, (2) Quantity of food to be ingested, and (3) macronutrients of food to be ingested. Erroneous estimates of any of these three values can lead to unexpected glucose response of a subject's body to the stimuli's of a control system (via insulin, or other hormones such as glucagon or epinephrine). Typically, hybrid closed loop out-performs reactive closed loop by 15% via time in range (TIR). However, there are cases where users will knowingly choose to fool the system to wrongly administer insulin, erroneously input one of the 3 meal factors, or forget to notify the system altogether. With the addition of a lipid measurement, such as triglycerides, the time of meal can be determined to within a 15-minute window. As a result, a model start time can be corrected. Retrospectively, the quantity and macronutrients can also be corrected to improve the function and reliability of a control algorithm (such as a Model Predictive Control (MPC) forecasting some amount of time into the future). In another example, ketones could additionally or alternatively be measured and re-incorporated into protein macro corrections.

Additional benefits of lipid measurements occur when used in reactive closed loop control. Triglycerides and chylomicron are known to have statistically significant spikes within 30 minutes of glucose entering the stomach. This timing is in lockstep with timing of insulin release in a normal healthy subject. With the increase of lipid analytes, a reactive closed loop algorithm could advantageously release large doses of insulin up to 45 minutes earlier which would enable a TIR that may be expected for a well estimated hybrid closed loop meal entry. This method could also retrospectively augment the MPC forecasting some time into the future.

Chylomicron reservoirs must be quantified to realize if it is available to release into a subject's blood stream for accurate meal response insulin dosing. If chylomicron reservoirs were to be empty, then no spike would be observed by a Continuous Analyte Monitor (CAM) even though a meal has taken place. This would result in an under-dosing of insulin allowing a user's blood sugar to increase out of range. This is a relatively harmless result in the short term of a user's health outcomes. Therefore, it may be advantageous to switch between lipid-information-using and traditional closed loop algorithms should the chylomicron reservoir become exhausted.

A control system may determine a chylomicron reservoir using a chylomicron reservoir estimation method. The chylomicron reservoir estimation method may be based on past meals input and/or past lipid spikes to assess whether an individual still has chylomicron ready to be observed for a meal response as presented (for example, by a user). In some examples, starch and water may be excluded.

Such a lipid measurement and re-estimation of meal dosing factors could be used to improve the confidence intervals over which a model could be evaluated on. Meal dosing factors may include but are not limited to (1) start time of food ingestion, (2) Quantity of food to be ingested, and (3) macronutrients of food to be ingested. This could be used to present a user with a dynamically improved confidence interval of non-invasive, invasive, or simulated glucose predictions retrospectively, at time of measurement, or in a forecasted manner. This would produce a highly beneficial effect on the user's outcome and overall system performance.

K. Glucagon in Closed Loop Control

Glucagon is a major hormone in the body that is similar to insulin. It encourages release of glucose into the blood systemically as opposed to insulin which removes it. It can be useful as a tool to help during emergency hypoglycemic events but is seldom used. Two reasons which glucagon is not more frequently used are: (1) Using a glucagon pen promotes the feeling of "infantilism" in which the dying user feels dependent on other people to save their life and therefore as if they cannot live a singular life and (2) Glucagon creates vomiting in many cases of administration.

Current CGMs may not produce very accurate control due to lag-time issues between plasma and interstitial fluid glucose. Additionally, control algorithms in current CGMS may produce false-alarms due to inaccuracy. Some manufacturers require alarms that cannot be silenced, resulting in annoyance and sleep disturbance for users. One way of addressing this issue is by mitigating the issue of hypoglycemia. Alarms are set very high because a subject can only manage their state if they are conscious. If a device were to have a failsafe measure to manage the hypoglycemic state, one could argue the limit could be brought lower and remove a significant number of false alarms.

In some examples, a control system may include an emergency glucagon dispensing system. Using an emergency glucagon system activation, the threshold for alarm can be safely lowered to significantly reduce false-alarms and chance of death when assuming, for example, a maximum possible physiologic rate of change of glucose of −3 [mg/dL]. The time to react is related to the time to wake up, take a validation measurement while possibly impaired, and administer a lifesaving emergency glucagon syringe before losing consciousness (which may occur at around 20 [mg/dL]). A threshold may be conservatively determined around the approximate reaction time for the system or user. The minimum glucose that would be reached is based on a predictive glucose model, such as a glucose-insulin-meal model, that overdosed insulin after a meal and triggered a 2-unit emergency glucagon system.

There are moments when an emergency glucagon system cannot be activated, and in those moments the threshold may be raised. The quantification of high threshold states and low threshold states is discussed below. There is up to a 36% probability glucagon can induce nausea and 18% probability for inducing vomiting. Therefore, position of a user when administering glucagon can be important for safety in order to prevent airway obstruction due to vomiting. Body position should not include a state where a user is likely to have an airway obstruction in the case of vomiting. As a result, an emergency glucagon system may be coupled with an accelerometer. The orientation of the device on the user's body could be quantified. The orientation of the users during sleep would be quantified relative to the orientation of the device on the user's body during sleep as described in the four states—(a) side, (b) back, (c) stomach, and (d) out of scope. A description of an emergency glucagon system is described in application Ser. No. 17/344,342, titled EMERGENCY GLUCAGON SYSTEM, filed Jun. 10, 2021, which is hereby incorporated by reference herein.

L. Graphical User Interface

In some examples, a controller 1000 may be configured to receive inputs or communicate outputs to and from a user through a user mobile device or application configured to run on a mobile device, other computing device or web interface. In some examples, controller 1000 may be configured to interface with the user through a graphical user interface.

For example, a graphical user interface may include indicators for connectivity of at least one medical control device, such as a combination glucose sensing and insulin delivery or other device such as described above with reference to FIGS. 1A-1D.

In some examples, a graphical user interface may include physiological measurement information, including but not limited to glucose, insulin, carbohydrate intake, and activity level. In some examples, the measurement information may be displayed in a graphical and/or textual format. For example, measurement information may be displayed over time in a line graph or other time-based graph. In addition or in the alternative, measurement information may be displayed textually. In some examples, event information, such as an insulin bolus, meal bolus, or activity event, may be displayed so as to allow a user to perceive when an event occurred in relation to the measurement information. In some examples, trend information may be displayed, such as a rising or falling glucose value. In some examples, a prediction may be displayed, such as a predicted rise or fall of glucose.

In some examples, a graphical user interface may include inputs for insulin information, meal information, activity information, or other user input information. In some examples, an input may be tied to an action of a device in a control system environment. For example, a user may input an insulin bolus by manually requesting an insulin bolus through the graphical user interface. The controller 1000 may then cause the bolus to be administered and record the bolus as an input. In some examples, a graphical user interface may allow a user to input past or future values of a bolus or other input, such as an anticipated meal or activity or past meal or activity. In some examples, a graphical user interface may be configured to allow a user to input glucose or other analyte values separately measured from a connected device. For example, a graphical user interface may allow a user to input a glucose meter value in addition or in the alternative to measured glucose values from a connected glucose sensing device. In another example, a graphical user interface may allow inputs from an analyte measuring device. In some examples, a graphical user interface may allow a user to input insulin information associated with insulin in a device reservoir (such as an insulin type and/or amount) or associated with separately administered insulin. In some examples, a graphical user interface may allow a user to input an insulin bolus (along with information associated with the bolus, such as amount and/or type of insulin) and record that as a bolus event. In some examples, other input information may also be recorded through the graphical user interface, such as the use of glucagon or other medication. A controller 1000 may be configured to utilize the separately input values or directly measured values in making predictions or for other processes of a control system environment 100.

In some examples, a graphical user interface may be configured to output an alert (in addition or in the alternative to an alert on a device itself or to a third party or other network connected device). For example, if a glucose prediction engine 1004 predicts a hypoglycemic event, a graphical user interface may emit an audible, haptic, and/or visual alert to the user. In another example, if a controller 1000 anticipates an anticipated empty state of one or more insulin reservoirs, the controller 1000 may cause the graphical user interface to output an alert (in addition or in the alternative to an alert on a device itself or to a third party or other network connected device). In some examples, a controller 1000 may cause an alert where one or more medical control devices has encountered an error, failed, or otherwise has reduced functionality. In some examples, a graphical user interface may be configured to allow a user to snooze, dismiss, reset, or modify settings associated with an alert.

In some examples, a graphical user interface may be configured to allow a user to set up a new device or reconnect a device. In some examples, a graphical user interface may be configured to authenticate a user using one or more authentication techniques, such as a password, PIN, biometric authentication, or other form of authentication, such as is available to the user based on the device they are using to access the graphical user interface or through the medical control device itself. In some examples, a controller 1000 may be configured to identify and authorize a user to access certain aspects of a graphical user interface based on a determined level of access. For example, a controller 1000 may allow an authorized user to modify an insulin level manually if they have a certain level of access.

In some examples, a graphical user interface may allow a user to set one or more profiles associated with settings of aspects of the graphical user interface and/or control system environment 100. In some examples, settings may include permissions for caregivers, healthcare providers, 3rd party applications or devices, and other permissions.

M. Additional Examples

Disclosed herein are additional examples of a closed loop control system. Any of the examples disclosed herein may be combined in whole or in part.

Example 1: A glucose control system comprising:

a glucose sensor;

an insulin pump; and one or more hardware processors configured to execute instructions to:

determine a first connectivity of the hardware processor to a mobile computing device;

determine a second connectivity of the mobile computing device to one or more remote hardware processors; and select a control process among a plurality of control processes for operation of the at least one insulin administration system based on the first connectivity and the second connectivity.

Example 2: The glucose control system of Example 1, wherein the first connectivity comprises an active Bluetooth connection.

Example 3: The glucose control system of Example, 1, wherein the second connectivity comprises an active internet connection.

Example 4: The glucose control system of Example 1, wherein to select a control process, the one or more hardware processors are configured to:

select a first control process for operation of the at least one insulin administration system if the first connectivity is an active connected state and the second connectivity is an active connected state.

Example 5: The glucose control system of Example 4, wherein the first control process comprises a predictive control algorithm associated with a physiological model of the glycemic response of the user.

Example 6: The glucose control system of Example 5, wherein the predictive control algorithm comprises a model predictive control algorithm.

Example 7: The glucose control system of Example, 4, wherein the first control process is configured to recommend insulin dosage based on a glucose prediction determined using inputs comprising meal intake and insulin bolus.

Example 8: The glucose control system of Example 4, wherein the first control process is configured to recommend an insulin dosage based on a current or predicted glucose state.

Example 9: The glucose control system of Example 4, wherein the one or more hardware processors are configured to:

receive a recommended insulin dosage from the one or more remote hardware processors based on inputs, the inputs comprising meal intake and insulin bolus; and output the recommended insulin dosage to the at least one insulin administration system.

Example 10: The glucose control system of Example 1, wherein to select a control process, the one or more hardware processors are configured to:

select a second control process for operation of the at least one insulin administration system if the first connectivity is an active connected state and the second connectivity is a disconnected state.

Example 11: The glucose control system of Example 10, wherein the one or more hardware processors are configured to determine a recommended insulin dosage based on one or more user inputs or measured glucose.

Example 12: The glucose control system of example 11, wherein the one or more user inputs comprise at least one of: meal intake, exercise, sleep, mood, or anticipated event.

Example 13: The glucose control system of Example 1, wherein to select a control process, the one or more hardware processors are configured to: select a third control process for operation of the at least one insulin administration system if the first connectivity is a disconnected state and the second connectivity is a disconnected state.

Example 14: The glucose control system of Example 13, wherein the third control process is configured to output an insulin dosage based on a reactive glucose model.

Example 15: The glucose control system of Example 13, wherein the third control process is a default operation of the insulin administration system.

Example 16: The glucose control system of Example 13, wherein the insulin administration system comprises at least one device comprising a combination insulin pump and glucose sensing device.

Example 17: The glucose control system of Example 1, wherein the glucose sensor and the insulin pump are integrated into a single device.

Example 18: The glucose control system of Example 1, wherein the one or more hardware processors are embedded in the glucose sensor.

Example 19: A method of selecting a control process for an insulin administration system, the method comprising:

determining a first connection state between at least one glucose control system and at least one mobile computing device;

changing a control state of the at least one glucose control system to a second control state from a default control state if the first connection state is active;

determining a second connection state between the at least one mobile computing device and a cloud computing system; and changing the control state to a third control state if both the first connection state and the second connection state is active.

Example 20: The method of Example 19 comprising:

if the control state is the second control state:

synchronize at least one user input value between the at least one mobile computing device and the insulin administration system; and calculate a glucose prediction based on the at least one user input value.

Example 21: The method of Example 19 comprising: if the control state is the third control state:

synchronize at least one value between the at least one mobile computing device and the cloud computing system; and receive a glucose prediction from the cloud computing system.

Example 22: A user authentication system for a glucose control system, the system comprising:

at least one insulin administration system comprising:

a glucose sensor; and an insulin pump;

one or more hardware processors configured to execute instructions to:

receive, from a user input device, a request to update a control value associated with the at least one insulin administration system;

determine an authorization level associated with a user of the user input device; and allow or deny the update based on the authorization level.

Example 23: The user authentication system of Example 22, wherein the authorization level comprises permission to override, observe, or update to update at least one control value.

Example 24: The user authentication system of Example 22, wherein the authorization level is based on a user age.

Example 25: The user authentication system of Example 22, wherein the authorization level is different for a managing user, healthcare provider user, and patient user.

Example 26: A glucose control system comprising:

a glucose sensor;

an insulin pump; and one or more hardware processors configured to execute instructions to:

receive one or more inputs for a predictive glucose model;

analyze the one or more inputs and one or more historical glucose values and historical inputs to determine a pattern of insulin response; and update the predictive glucose model with the one or more inputs based on the pattern of insulin response.

Example 27: The glucose control system of Example 26, wherein the predictive glucose model comprises a generic physiological glucose model based on a plurality of people.

Example 28: The glucose control system of Example 26, wherein the predictive glucose model comprises a physiological model personalized to the user.

Example 29: The glucose control system of Example 26, wherein the pattern of insulin response comprises an insulin response over a predicted estimate and wherein the updated predictive glucose model lowers an insulin dosage.

Example 30: The glucose control system of Example 26, wherein the pattern of insulin response comprises an insulin response below a predicted estimate and wherein the updated predictive glucose model increases an insulin dosage.

Example 31: The glucose control system of Example 26, wherein the one or more hardware processors are configured to execute instructions to analyze the one or more inputs and the one or more historical glucose values and historical inputs to determine a user behavior pattern.

Example 32: The glucose control system of Example 31, wherein the one or more hardware processors are configured to execute instructions to update the predictive glucose model based on the pattern of user behavior.

Example 33: The glucose control system of Example 26, wherein the one or more hardware processors are configured to execute instructions to analyze a measured glucose value to determine a missed input value.

Example 34: The glucose control system of Example 33, wherein the one or more hardware processors are configured to execute instructions to update the predictive glucose model based on the missed input value.

Example 35: The glucose control system of Example 26, wherein the one or more hardware processors are embedded in the glucose sensor.

Example 36: The glucose control system of Example 26, wherein the glucose sensor and insulin pump are integrated into a single device.

Example 37: A glucose control system comprising:

a glucose sensor;

an insulin pump; and one or more hardware processors configured to execute instructions to:

determine a first set of parameters for a predictive glucose model;

receive a first measured physiological parameter;

analyze a set of user inputs and the first measured physiological parameter to determine the presence of a missed or erroneous input value;

update the first set of parameters for the predictive glucose model to a second set of parameters based on the with the one or more inputs based on the missed or erroneous input value;

generate a glucose prediction value based on the second set of parameters; and output an insulin bolus recommendation to the at least one insulin administration system based on the glucose prediction value.

Example 38: The glucose control system of Example 36, wherein the first set of parameters are determined based on a plurality of people.

Example 39: The glucose control system of Example 36, wherein the first set of parameters are personalized to the user.

Example 40: The glucose control system of Example 36, wherein the first measured physiological parameter comprises a glucose measurement from the glucose sensor.

Example 41: The glucose control system of Example 36, wherein the first measured physiological parameter comprises a ketone value.

Example 42: The glucose control system of Example 36, wherein the first measured physiological parameter comprises a lipid measurement.

Example 43: The glucose control system of Example 41, wherein the lipid measurement comprises a triglyceride value.

Example 44: The glucose control system of Example 36, wherein the one or more hardware processors are configured to determine a chylomicron reservoir based on past meal input or past lipid measurements.

Example 45: The glucose control system of Example 40, wherein to analyze a set of user inputs and the first measured physiological parameter to determine the presence of a missed or erroneous input value, the one or more hardware processors are configured to:

determine a confidence score associated with a meal intake based on the chylomicron reservoir; and identify the presence of a missed or erroneous input value based on the confidence score.

Example 46: The glucose control system of Example 40, wherein the confidence score is associated with at least one meal dosing factor, the at least one meal dosing factor at least one of: start time of the meal intake, quantity of food associated with the meal intake, or macronutrients associated with the meal intake.

Example 47: A glucose control system comprising:

a glucose sensor;

an insulin pump; and one or more hardware processors configured to execute instructions to:

receive a user input, the user input comprising meal intake and insulin intake;

determine a first glucose prediction using an empirical model based on the user input;

receive a measured glucose value;

update the empirical model based on the measured glucose value and the user input; and output an insulin bolus recommendation to the at least one insulin administration system based on the second glucose prediction value.

Example 48: The glucose control system of Example 47 wherein the empirical model comprises an autoregressive model with exogenous input.

Example 49: The glucose control system of Example 47, wherein the one or more hardware processors are embedded in the glucose sensor.

Example 50: The glucose control system of Example 47, wherein the glucose sensor and insulin pump are integrated into a single device.

Example 51: A glucose control system comprising:

a glucose sensor;

an insulin pump;

a glucagon administration system; and one or more hardware processors configured to execute instructions to:

receive a measured glucose value from the at least one insulin administration system;

determine if the measured glucose value falls below a threshold value;

determine an orientation of the user; and administer glucagon to a user using the glucagon administration system based on the orientation of the user and a determination that the measured glucose value falls below the threshold value.

Example 52: The glucose control system of Example 51, wherein the one or more hardware processors are configured to administer glucagon if an orientation of the user is standing or on their stomach.

Example 53: The glucose control system of Example 51, wherein the one or more hardware processors are configured to determine an orientation of the user by: determining an orientation of the glucagon administration system based on an inertial measurement sensor.

Example 54: The glucose control system of Example 51, wherein the inertial measurement sensor comprises an accelerometer.

Example 55: The glucose control system of Example 51, wherein the inertial measurement sensor comprises a gyroscope.

Example 57: A glucose control system comprising:

a glucose sensor;

at least one medication administration system; and one or more hardware processors configured to execute instructions to:

determine a first connectivity of the hardware processor to a mobile computing device;

determine a second connectivity of the mobile computing device to one or more remote hardware processors; and select a control process among a plurality of control processes for operation of the at least one medication administration system based on the first connectivity and the second connectivity.

Example 58: The glucose control system of any of the above Examples, wherein the first connectivity comprises an active Bluetooth connection.

Example 59: The glucose control system any of the above Examples, wherein the second connectivity comprises an active internet connection.

Example 60: The glucose control system of any of the above Examples, wherein to select a control process, the one or more hardware processors are configured to:

select a first control process for operation of the at least one medication administration system if the first connectivity is an active connected state and the second connectivity is an active connected state.

Example 61: The glucose control system of any of the above Examples, wherein the first control process comprises a predictive control algorithm associated with a physiological model of a glycemic response of a user.

Example 62: The glucose control system of any of the above Examples, wherein the predictive control algorithm comprises a model predictive control algorithm.

Example 63: The glucose control system of any of the above Examples, wherein the first control process is configured to recommend medication dosage based on a glucose prediction determined using inputs comprising meal intake and medication bolus.

Example 64: The glucose control system of any of the above Examples, wherein the first control process is configured to recommend a medication dosage based on a current or predicted glucose state.

Example 65: The glucose control system of any of the above Examples, wherein the one or more hardware processors are configured to:

receive a recommended medication dosage from the one or more remote hardware processors based on inputs, the inputs comprising meal intake and medication bolus; and output the recommended medication dosage to the at least one medication administration system.

Example 66: The glucose control system of any of the above Examples, wherein to select a control process, the one or more hardware processors are configured to:

select a second control process for operation of the at least one medication administration system if the first connectivity is an active connected state and the second connectivity is a disconnected state.

Example 67: The glucose control system of any of the above Examples, wherein the one or more hardware processors are configured to determine a recommended medication dosage based on one or more user inputs or measured glucose.

Example 68: The glucose control system of any of the above Examples, wherein the one or more user inputs comprise at least one of: meal intake, exercise, sleep, mood, or anticipated event.

Example 69: The glucose control system of any of the above Examples, wherein to select a control process, the one or more hardware processors are configured to:

select a third control process for operation of the at least one medication administration system if the first connectivity is a disconnected state and the second connectivity is a disconnected state.

Example 70: The glucose control system of any of the above Examples, wherein the third control process is configured to output a medication dosage based on a reactive glucose model.

Example 71: The glucose control system of any of the above Examples, wherein the third control process is a default operation of the medication administration system.

Example 72: The glucose control system of any of the above Examples, wherein the medication administration system comprises at least one device comprising a combination medication delivery system and glucose sensing device.

Example 73: The glucose control system of any of the above Examples, wherein the glucose sensor and the medication administration system are integrated into a single device.

Example 74: The glucose control system of any of the above Examples, wherein the one or more hardware processors are embedded in the glucose sensor.

Example 75: A method of selecting a control process for a medication administration system, the method comprising:

determining a first connection state between at least one glucose control system and at least one mobile computing device;

changing a control state of the at least one glucose control system to a second control state from a default control state if the first connection state is active;

determining a second connection state between the at least one mobile computing device and a cloud computing system; and changing the control state to a third control state if both the first connection state and the second connection state is active.

Example 76: The method of any of the above Examples comprising: if the control state is the second control state:

synchronize at least one user input value between the at least one mobile computing device and the medication administration system; and calculate a glucose prediction based on the at least one user input value.

Example 77: The method of any of the above Examples comprising: if the control state is the third control state:

synchronize at least one value between the at least one mobile computing device and the cloud computing system; and receive a glucose prediction from the cloud computing system.

Example 78: A user authentication system for a glucose control system, the system comprising:

at least one medication administration system comprising:

a glucose sensor; and a medication administration system;

one or more hardware processors configured to execute instructions to:

receive, from a user input device, a request to update a control value associated with the at least one medication administration system;

determine an authorization level associated with a user of the user input device; and allow or deny the update based on the authorization level.

Example 79: The user authentication system of any of the above Examples, wherein the authorization level comprises permission to override, observe, or update to update at least one control value.

Example 80: The user authentication system of any of the above Examples, wherein the authorization level is based on a user age.

Example 81: The user authentication system of any of the above Examples, wherein the authorization level is different for a managing user, healthcare provider user, and patient user.

Example 82: A glucose control system comprising:

a glucose sensor;

medication administration system; and one or more hardware processors configured to execute instructions to:

receive one or more inputs for a predictive glucose model;

analyze the one or more inputs and one or more historical glucose values and historical inputs to determine a pattern of medication response; and update the predictive glucose model with the one or more inputs based on the pattern of medication response.

Example 83: The glucose control system of any of the above Examples, wherein the predictive glucose model comprises a generic physiological glucose model based on a plurality of people.

Example 84: The glucose control system of any of the above Examples, wherein the predictive glucose model comprises a physiological model personalized to a user of the glucose control system.

Example 85: The glucose control system of any of the above Examples, wherein the pattern of medication response comprises a medication response over a predicted estimate and wherein the updated predictive glucose model lowers a medication dosage.

Example 86: The glucose control system of any of the above Examples, wherein the pattern of medication response comprises a medication response below a predicted estimate and wherein the updated predictive glucose model increases a medication dosage.

Example 87: The glucose control system of any of the above Examples, wherein the one or more hardware processors are configured to execute instructions to analyze the one or more inputs and the one or more historical glucose values and historical inputs to determine a user behavior pattern.

Example 88: The glucose control system of any of the above Examples, wherein the one or more hardware processors are configured to execute instructions to update the predictive glucose model based on the pattern of user behavior.

Example 89: The glucose control system of any of the above Examples, wherein the one or more hardware processors are configured to execute instructions to analyze a measured glucose value to determine a missed input value.

Example 90: The glucose control system of any of the above Examples, wherein the one or more hardware processors are configured to execute instructions to update the predictive glucose model based on the missed input value.

Example 91: The glucose control system of any of the above Examples, wherein the one or more hardware processors are embedded in the glucose sensor.

Example 92: The glucose control system of any of the above Examples, wherein the glucose sensor and medication administration system are integrated into a single device.

Example 93: A glucose control system comprising:

a glucose sensor;

at least one medication administration system; and one or more hardware processors configured to execute instructions to:

determine a first set of parameters for a predictive glucose model;

receive a first measured physiological parameter;

analyze a set of user inputs and the first measured physiological parameter to determine a presence of a missed or erroneous input value;

update the first set of parameters for the predictive glucose model to a second set of parameters based on the with the one or more inputs based on the missed or erroneous input value;

generate a glucose prediction value based on the second set of parameters; and output a medication bolus recommendation to the at least one medication administration system based on the glucose prediction value.

Example 94: The glucose control system of any of the above Examples, wherein the first set of parameters are determined based on a plurality of people.

Example 95: The glucose control system of any of the above Examples, wherein the first set of parameters are personalized to the user.

Example 96: The glucose control system of any of the above Examples, wherein the first measured physiological parameter comprises a glucose measurement from the glucose sensor.

Example 97: The glucose control system of any of the above Examples, wherein the first measured physiological parameter comprises a ketone value.

Example 98: The glucose control system of any of the above Examples, wherein the first measured physiological parameter comprises a lipid measurement.

Example 99: The glucose control system of any of the above Examples, wherein the lipid measurement comprises a triglyceride value.

Example 100: The glucose control system of any of the above Examples, wherein the one or more hardware processors are configured to determine a chylomicron reservoir based on past meal input or past lipid measurements.

Example 101: The glucose control system of any of the above Examples, wherein to analyze a set of user inputs and the first measured physiological parameter to determine a presence of a missed or erroneous input value, the one or more hardware processors are configured to:

determine a confidence score associated with a meal intake based on the chylomicron reservoir; and identify the presence of a missed or erroneous input value based on the confidence score.

Example 102: The glucose control system of any of the above Examples, wherein the confidence score is associated with at least one meal dosing factor, the at least one meal dosing factor at least one of: start time of the meal intake, quantity of food associated with the meal intake, or macronutrients associated with the meal intake.

Example 103: A glucose control system comprising:

a glucose sensor;

at least one medication administration system; and one or more hardware processors configured to execute instructions to:

receive a user input, the user input comprising meal intake and medication intake;

determine a first glucose prediction using an empirical model based on the user input;

receive a measured glucose value;

update the empirical model based on the measured glucose value and the user input; and output a medication bolus recommendation to the at least one medication administration system.

Example 104: The glucose control system of any of the above Examples wherein the empirical model comprises an autoregressive model with exogenous input.

Example 105: The glucose control system of any of the above Examples, wherein the one or more hardware processors are embedded in the glucose sensor.

Example 106: The glucose control system of any of the above Examples, wherein the glucose sensor and medication administration system are integrated into a single device.

Example 107: A glucose control system comprising:

a glucose sensor;

at least one medication administration system;

a glucagon administration system; and one or more hardware processors configured to execute instructions to:

receive a measured glucose value from the at least one medication administration system;

determine if the measured glucose value falls below a threshold value;

determine an orientation of a user; and administer glucagon to a user using the glucagon administration system based on the orientation of the user and a determination that the measured glucose value falls below the threshold value.

Example 108: The glucose control system of any of the above Examples, wherein the one or more hardware processors are configured to administer glucagon if an orientation of the user is standing or on their stomach.

Example 109: The glucose control system of any of the above Examples, wherein the one or more hardware processors are configured to determine an orientation of the user by: determining an orientation of the glucagon administration system based on an inertial measurement sensor.

Example 110: The glucose control system of any of the above Examples, wherein the orientation of the user is based on at least one signal from at least one inertial measurement sensor.

Example 111: The glucose control system of any of the above Examples, wherein the at least one inertial measurement sensor comprises an accelerometer.

Example 112: The glucose control system of any of the above Examples, wherein the at least one inertial measurement sensor comprises a gyroscope.

Example 113: A method of using any of the above disclosed systems.

Example 114: A system using any of the above disclosed methods.

N. Alternative Applications

While the disclosure herein refers primarily to glucose control through administration of insulin in a closed loop or similar system, the control system described above may relate to other applications. For example, a similar such system could be used in the administration of blood thinners if the control variable of viscosity or blood thinning related analytes concentrations could be determined in real time. A similar such system could be used in the administration of narcotics or anesthesia if the control variable of narcotic concentration, pain, or consciousness could be determined in real time.

In some examples, a medical control device status may be communicated to the user through the graphical user interface (in addition or in the alternative to on the device). For example, if a device is not connected, a symbol representing a device may be grayed out and/or dashed. If a device is connected and working, a symbol representing a device may be green at least in part. If a device is experiencing an alert state, a symbol representing a device may be yellow at least in part. In a device is experiencing an alarm state, a symbol representing a device may be red at least in part. In examples where a control system environment 100 includes a primary and a secondary medical control device, such as described above with reference to FIGS. 1A-1D, a control state and/or connectivity of a device may be communicated to a user through the display of symbols corresponding to the medical control devices. For example, if device symbols are shown as overlapping, a control state may be, for example, a tier 1 algorithm or closed loop control. If device symbols are shown as separated, a control state may be, for example, an open loop control.

O. Terminology

Conditional language used herein, such as, among others, "can," "could," "might," "may," "e.g.," and the like, unless specifically stated otherwise, or otherwise understood within the context as used, is generally intended to convey that certain, certain features, elements and/or steps are optional. Thus, such conditional language is not generally intended to imply that features, elements and/or steps are in any way required or that one or more implementations necessarily include logic for deciding, with or without other input or prompting, whether these features, elements and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid-state memory chips and/or magnetic disks, into a different state. The computer system may be a cloud-based computing system whose processing resources are shared by multiple distinct business entities or other users.

Depending on the implementation, certain acts, events, or functions of any of the processes or algorithms described herein can be performed in a different sequence, can be added, merged, or left out altogether (for example, not all described operations or events are necessary for the practice of the algorithm). Moreover, in certain implementations, operations or events can be performed concurrently, for example, through multi-threaded processing, interrupt processing, or multiple processors or processor cores or on other parallel architectures, rather than sequentially.

The various illustrative logical blocks, modules, routines, and algorithm steps described in connection with the disclosure herein can be implemented as electronic hardware (for example, ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the disclosure herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor device can be a microprocessor, but in the alternative, the processor device can be a controller, microcontroller, or state machine, combinations of the same, or the like. A processor device can include electrical circuitry configured to process computer-executable instructions. A processor device can include an FPGA or other programmable device that performs logic operations without processing computer-executable instructions. A processor device can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the disclosure herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A glucose control system comprising:
- a glucose sensor;
- at least one medication administration system; and
- one or more local hardware processors configured to execute instructions to:
  - determine a first connectivity state between the one or more local hardware processors and a mobile computing device;
  - determine a second connectivity state between the mobile computing device and one or more remote hardware processors; and
  - select a control process from among a plurality of control processes for operation of the at least one medication administration system based on the first connectivity state and the second connectivity state,
  - wherein each of the plurality of control processes determines an amount of medication to administer using a different control logic associated with a distinct combination of the first and second connectivity states, and
  - wherein the selection of the control process is performed as a function of the first connectivity state and second connectivity state.

2. The glucose control system of claim 1, wherein the first connectivity state comprises an active Bluetooth connection.

3. The glucose control system of claim 1, wherein the second connectivity state comprises an active internet connection.

4. The glucose control system of claim 1, wherein to select a control process, the one or more hardware processors are configured to:
- select a first control process for operation of the at least one medication administration system if the first connectivity is an active connected state and the second connectivity is an active connected state.

5. The glucose control system of claim 4, wherein the first control process comprises a predictive control algorithm associated with a physiological model of a glycemic response of a user.

6. The glucose control system of claim 5, wherein the predictive control algorithm comprises a model predictive control algorithm.

7. The glucose control system of claim 4, wherein the first control process is configured to recommend medication dosage based on a glucose prediction determined using inputs comprising meal intake and medication bolus.

8. The glucose control system of claim 4, wherein the first control process is configured to recommend a medication dosage based on a current or predicted glucose state.

9. The glucose control system of claim 4, wherein the one or more hardware processors are configured to:
- receive a recommended medication dosage from the one or more remote hardware processors based on inputs, the inputs comprising meal intake and medication bolus; and
- output the recommended medication dosage to the at least one medication administration system.

10. The glucose control system of claim 1, wherein to select a control process, the one or more hardware processors are configured to:
- select a second control process for operation of the at least one medication administration system if the first connectivity is an active connected state and the second connectivity is a disconnected state.

11. The glucose control system of claim 10, wherein the one or more hardware processors are configured to determine a recommended medication dosage based on one or more user inputs or measured glucose.

12. The glucose control system of claim 11, wherein the one or more user inputs comprise at least one of: meal intake, exercise, sleep, mood, or anticipated event.

13. The glucose control system of claim 1, wherein to select a control process, the one or more hardware processors are configured to:
- select a third control process for operation of the at least one medication administration system if the first connectivity is a disconnected state and the second connectivity is a disconnected state.

14. The glucose control system of claim 13, wherein the third control process is configured to output a medication dosage based on a reactive glucose model.

15. The glucose control system of claim 13, wherein the third control process is a default operation of the medication administration system.

16. The glucose control system of claim 13, wherein the medication administration system comprises at least one device comprising a combination medication delivery system and glucose sensing device.

17. The glucose control system of claim 1, wherein the glucose sensor and the medication administration system are integrated into a single device.

18. The glucose control system of claim 1, wherein the one or more hardware processors are embedded in the glucose sensor.

* * * * *